US008247439B2

(12) United States Patent
Herzberg et al.

(10) Patent No.: US 8,247,439 B2
(45) Date of Patent: Aug. 21, 2012

(54) JASMONATE DERIVATIVES, PHARMACEUTICAL COMPOSITIONS AND METHODS OF USE THEREOF

(75) Inventors: Max Herzberg, Sitrya (IL); Adrian Harel, Ness Ziona (IL); Christian Mang, Berlin (DE)

(73) Assignee: Sepal Pharma Ltd., Ness-Ziona (IL)

( * ) Notice: Subject to any disclaimer, the term of this patent is extended or adjusted under 35 U.S.C. 154(b) by 867 days.

(21) Appl. No.: 12/096,111

(22) PCT Filed: Dec. 7, 2006

(86) PCT No.: PCT/IL2006/001409
§ 371 (c)(1),
(2), (4) Date: Sep. 30, 2008

(87) PCT Pub. No.: WO2007/066337
PCT Pub. Date: Jun. 14, 2007

(65) Prior Publication Data
US 2009/0197927 A1    Aug. 6, 2009

Related U.S. Application Data

(60) Provisional application No. 60/830,666, filed on Jul. 14, 2006, provisional application No. 60/772,582, filed on Feb. 13, 2006, provisional application No. 60/742,875, filed on Dec. 7, 2005.

(51) Int. Cl.
*A61K 31/425* (2006.01)
*C07D 277/60* (2006.01)
(52) U.S. Cl. .................... 514/367; 548/152
(58) Field of Classification Search .......... 514/367; 548/152
See application file for complete search history.

(56) References Cited

U.S. PATENT DOCUMENTS

| 5,476,945 | A | * | 12/1995 | Ikegawa et al. | 548/152 |
| 5,637,484 | A | | 6/1997 | Yukimune et al. | 435/123 |
| 6,469,061 | B1 | | 10/2002 | Flescher et al. | 210/640 |
| 6,861,431 | B2 | * | 3/2005 | Gudkov et al. | 514/252.1 |
| 7,402,602 | B2 | * | 7/2008 | Bigg et al. | 514/396 |

FOREIGN PATENT DOCUMENTS

| EP | 0683232 | 11/1995 |
| JP | 63-122669 A | 5/1988 |
| JP | 7-308196 A | 11/1995 |
| WO | WO 02/080890 | 10/2002 |
| WO | 2004/063155 A1 | 7/2004 |
| WO | WO 2005/054172 | 6/2005 |

OTHER PUBLICATIONS

Kramell et al., CAS: 111:39842, 1988.*
Berge SM. et al., "Pharmaceutical salts", *J Pharm Sci.*, 66(1):1-19 (Jan. 1977).
Buchwald H. et al., "Long-term, continuous intravenous heparin administration by an implantable infusion pump in ambulatory patients with recurrent venous thrombosis", *Surgery*, :88(4):507-516 (Oct. 1980).
Davies, P., Plant Hormones: Biosynthesis, Signal Transduction, Action!, Kluwer Academic Publishers, London, pp. 618-621 (2004).
Fingrut O. et al., "Plant stress hormones suppress the proliferation and induce apoptosis in human cancer cells", *Leukemia*, 16(4):608-616 (Apr. 2002).
Fingrut O. et al., "Jasmonates induce nonapoptotic death in high-resistance mutant p53—expressing B-lymphoma cells", *Br J Pharmacol.*, 146:800-808 (Nov. 2005).
Hossain SJ., "Fragrances in oolong tea that enhance the response of $GABA_A$ receptors". *Biosci Biotechnol Biochem.*, 68(9):1842-1848 (Sep. 2004).
Ishii et al., "Induction of differentiation of human myeloid leukemia cells by jasmonates, plant hormones", *Leukemia*, 18:1413-1419 (2004.
Jikumaru Y. et al., "Preparation and biological activity of molecular probes to identify and analyze jasmonic acid-binding proteins", *Biosci. Biotechnol. Biochem.*, 68(7):1461-1466 (Jul. 2004).
Kolho E. et al., "Hepatitis C antibodies in dialysis patients and patients with leukaemia", *J Med Virol.*, 40:318-321 (Aug. 1993).
Kuzuyama T. et al., "Cloning and expression in *Escherichia coli* of 2-hydroxypropylphosphonic acid epoxidase from the fosfomycin-producing organism, *Pseudomonas syringae* PB-5123", *Biosci. Biotechnol. Biochem.*, 63(12):2222-2224 (Dec. 1999).
Saudek CD et al, "A preliminary trial of the programmable implantable medication system for insulin delivery", *N Engl J Med.*, 321(9):574-579 (Aug. 31, 1989).
Ting A. et al., "Reactivity of autolymphocytotoxic antibodies from dialysis patients with lymphocytes from chronic lymphocytic leukemia (CLL) patients", *Transplantation*, 25(1):31-33. (Jan. 1978).
International Search Report for PCT/IL2006/001409 dated Oct. 5, 2007 (7 pages).
Written Opinion of the International Searching Authority for PCT/IL2006/001409 dated Oct. 5, 2007 (11 pages).
International Preliminary Report on Patentability for PCT/IL2006/001409 dated Jun. 11, 2008 (11 pages).
Japanese Office Action for corresponding Japanese Patent Application No. 2008-544003 dated Jun. 25, 2012 (English translation).

* cited by examiner

*Primary Examiner* — Rei-tsang Shiao
(74) *Attorney, Agent, or Firm* — Rodney J. Fuller; Booth Udall, PLC

(57) ABSTRACT

The present invention relates to novel jasmonate derivatives, methods for their preparation, pharmaceutical compositions including such compounds, and methods of using these compounds and compositions, especially as chemotherapeutic agents for prevention and treatment of cancers.

19 Claims, 6 Drawing Sheets

JASMONATE DERIVATIVES, PHARMACEUTICAL COMPOSITIONS AND METHODS OF USE THEREOF

RELATED APPLICATION DATA

This application is the U.S. national stage of PCT/IL2006/001409 filed on Dec. 7, 2006, which is based on and claims the benefit of U.S. provisional application Nos. 60/830,666 filed on Jul. 14, 2006; 60/772,582 filed on Feb. 13, 2006; and 60/742,875 filed on Dec. 7, 2005, the content of each of which is expressly incorporated herein in its entirety by reference hereto.

FIELD OF THE INVENTION

The present invention relates to the field of jasmonate derivative compounds, methods for their preparation, pharmaceutical compositions including such compounds, and methods of using these compounds and compositions, especially as chemotherapeutic agents for treatment of cancers especially in mammals, and particularly in humans.

BACKGROUND OF THE INVENTION

Jasmonates are a family of plant stress hormones, derived from linolenic acid by the octadecanoid pathway, which are found in minute quantities in many edible plants. Stress hormones such as the jasmonate family have evolved in plants, and are released in such times of stress such as extreme UV radiation, osmotic shock, heat shock and pathogen attack, to initiate various cascades which end in appropriate responses. Examples of members of the jasmonate family are jasmonic acid, which is crucial to intracellular signaling in response to injury, and methyl jasmonate, which causes induction of a proteinase inhibitor that accumulates at low concentrations in response to wounding or pathogenic attacks. Use of jasmonates for the treatment of mammalian cancer has been disclosed in U.S. Pat. No. 6,469,061, the contents of which are incorporated by reference in their entirety. In U.S. Pat. No. 6,469,061, it was shown that jasmonates were directly cytotoxic for various types of human cancer cells derived from breast, prostate, skin and blood cancers. While jasmonates elicited death in human leukemic Molt-4 cells, they did not damage normal lymphocytes.

In U.S. Pat. No. 6,469,061, one jasmonate compound in particular, methyl jasmonate, was shown to be effective in preventing development of lymphomas in mice. See also Fingrut, O. and E. Flescher. 2002. "Plant stress hormones suppress the proliferation and induce apoptosis in human cancer cells", Leukemia 16: 608-616 (2002).

Subsequent data collected similarly showed that jasmonates do not damage healthy erythrocytes (see WO 02/080890, the contents of which are incorporated by reference in their entirety).

PCT International Patent Publication WO 2005/054172 discloses novel halogenated jasmonate derivatives, pharmaceutical compositions comprising the derivatives, and their use for reducing cancer cell growth and for treating cancer.

Jasmonic acids conjugated via the carboxyl group to amino acids occur in nature (Plant Hormones, Davies P J, ed., Kluwer Academic Publishers, London, 2004, pp. 618, 620). Several jasmonic acid-amino acid conjugates have been synthetically prepared. The amino acids include glycine, alanine, valine, leucine and isoleucine. (Jikumaru Y. et al. Biosci. Biotechnol. Biochem. 68, 1461-1466, 2004). However, the therapeutic applications of these derivatives, e.g., for cancer treatment has not been previously described.

The pharmacological activity of jasmonate compounds makes them attractive candidates as therapeutic agents for the treatment of cancer. Because only a few jasmonate derivatives have been reported (see, for example, Ishii et al., Leukemia, 1-7 (2004); Hossain et al. Biochem. Biosci. & Biotech. 68(9), 1842 (2004)), a need in the art exists to develop jasmonate derivative compounds that are potent chemotherapeutic drugs, with a high degree of specificity towards malignant cells.

SUMMARY OF THE INVENTION

The present invention relates to novel jasmonate derivative compounds. Preferred jasmonate derivatives are thiazole derivatives represented by the structure of formula I. Other preferred jasmonate derivatives are compounds represented by the structure of formula IIA. Other preferred jasmonate derivatives are amino acid-jasmonate conjugates or peptide-jasmonate conjugates represented by the structure of formula II. Still other preferred jasmonate derivatives are oligomers represented by the structure of formulas IV, V or VI. Some of these compounds are significantly more potent than the compounds disclosed in U.S. Pat. No. 6,469,061 and WO 2005/054172. The novel derivatives exert selective cytotoxicity on cancerous cells, e.g. lymphocytes, carcinoma cells and breast cancer cells, while sparing normal cells. As such, the compounds of the present invention are useful in inhibiting cancer cell proliferation and treating and variety of cancers.

In one embodiment, the jasmonate derivatives are thiazole derivatives represented by the structure of formula I.

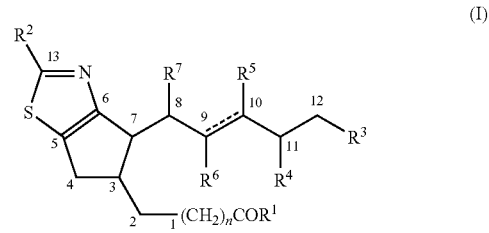

wherein
n is 0, 1, or 2;
$R^1$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, a natural or unnatural amino acid, a peptide, $OR^8$ and $NR^{9a}R^{9b}$;
$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, $NR^{9a}R^{9b}$, $NHCOR^{10}$ and $NHSO_2R^{11}$;
$R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;
wherein the bond between $C_9$ and $C_{10}$ can be a single or a double bond; and
$R^8$, $R^{9a}$, $R^{9b}$, $R^{10}$ and $R^{11}$, are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

In one currently preferred embodiment, $R^1$ in formula I is hydroxyl. In another embodiment, $R^1$ is methoxy. In yet another embodiment, $R^1$ is $NR^{9a}R^{9b}$, wherein $R^{9a}$ and $R^{9b}$ are as described in Formula I above. In another embodiment, $R^{9a}$ is hydrogen and $R^{9b}$ is selected from the group consisting of unsubstituted or substituted $C_1$-$C_{12}$ alkyl, unsubstituted or substituted $C_3$-$C_8$ cycloalkyl, unsubstituted or substituted aryl, and unsubstituted or substituted heteroaryl. In yet another embodiment, $R^{9a}$ and $R^{9b}$ together with the nitrogen to which they are attached form an unsubstituted or substituted heterocyclic or heteroaromatic ring optionally containing one or more additional heteroatom selected from O, N and S.

In one currently preferred embodiment, $R^2$ in Formula I is $NR^{9a}R^{9b}$ wherein $R^{9a}$ and $R^{9b}$ are as described in Formula I above. In another embodiment, $R^2$ is $NHCOR^{10}$ wherein $R^{10}$ is as described in Formula I above. In yet another embodiment, $R^2$ is $NHSO_2R^{11}$, wherein $R^{11}$ is as described in Formula I above. In one currently preferred embodiment, $R^2$ is phenyl. In another currently preferred embodiment, $R^2$ is $NHCOR^{10}$ wherein $R^{10}$ is a $C_1$-$C_{12}$ alkyl substituted with an aryl or heteroaryl (e.g., methylenethiophene).

In another currently preferred embodiment, each of $R^3$, $R^4$, $R^5$, $R^6$ and $R^7$ in Formula I is hydrogen. In another embodiment, the bond between $C_9$ and $C_{10}$ is a double bond, and each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen.

Specific examples of the compounds of formula I include but are not limited to:

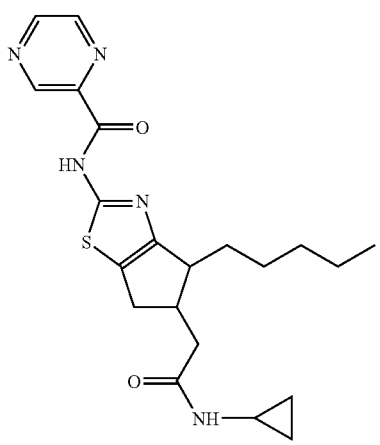

$A_1$

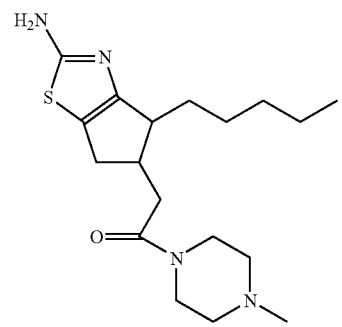

$A_2$

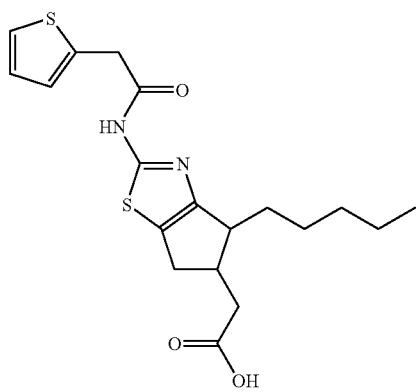

$A_3$

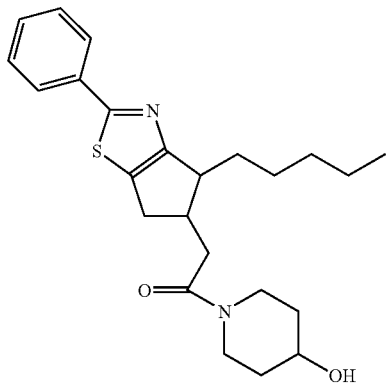

$A_4$

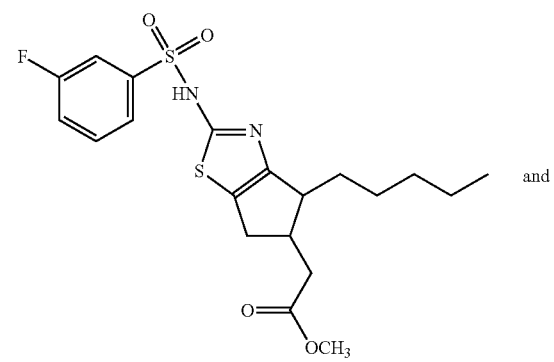

$A_5$

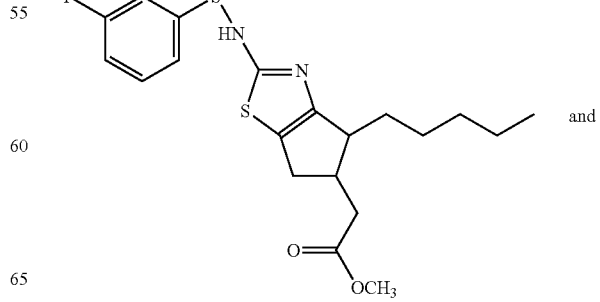

and

-continued

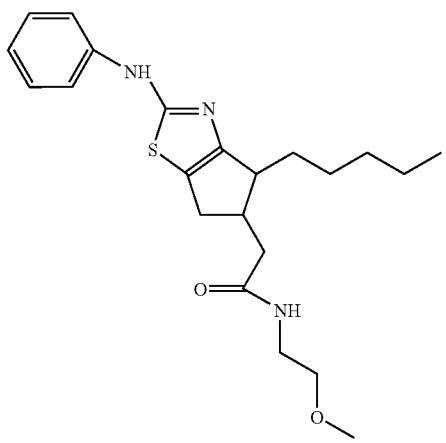

A<sub>6</sub>

In another aspect, the present invention relates to jasmonate derivatives represented by the structure of formula IIA.

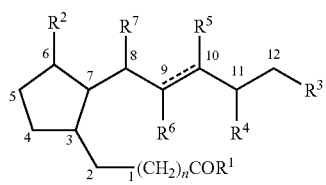

(IIA)

wherein
n is independently at each occurrence 0, 1, or 2;
$R^1$ is a group of the formula:

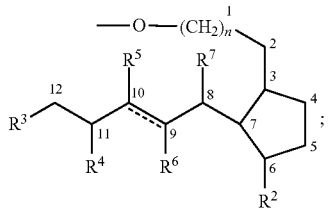

$R^2$ is independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently at each occurrence selected from the group consisting of hydrogen, unsubstituted or substituted $C_1$-$C_{12}$ allyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can independently at each occurrence be a single or a double bond; and $R^8$, $R^{9a}$ and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

In one embodiment, $R^1$ in the compound of formula IIA is a group of the formula:

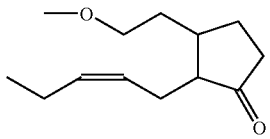

In a currently preferred embodiment, $R^2$ in the compound of formula IIA is oxo. In another currently preferred embodiment, each of $R^3$, $R^4$, $R^5$, $R^6$ and $R^7$ is hydrogen. In another embodiment, the bond between $C_9$ and $C_{10}$ is a double bond, and each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen.

A specific example of the compounds of the formula IIA is a compound of formula B3:

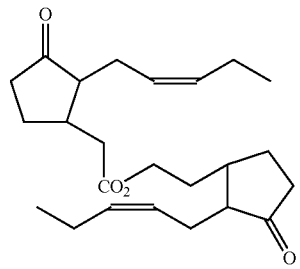

B<sub>3</sub>

In another aspect, the present invention relates to pharmaceutical compositions useful for the treatment of cancer, comprising a pharmaceutically acceptable carrier, and as an active ingredient a compound of structural formula IIB:

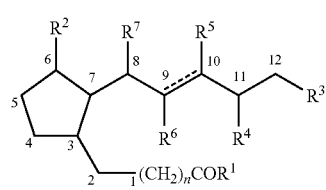

(IIB)

wherein
n is 0, 1, or 2;
$R^1$ is a natural or unnatural amino acid or a peptide;
$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can be a single or a double bond; and $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

The amino acid residue in the compounds of formula IIB can be a residue of any natural or unnatural amino acid. Currently preferred amino acids are leucine and tryptophan. However, any other natural and unnatural amino acid defined herein and known to a person of skill in the art can be incorporated into the jasmonate-amino acid derivatives of the present invention. Alternatively, the group $R^1$ can represent a peptide sequence comprising two or more amino acids, which can be natural amino acids, unnatural amino acids, or a combination thereof.

In a currently preferred embodiment, $R^2$ in the compound of formula IIB is oxo. In another currently preferred embodiment, each of $R^3$, $R^4$, $R^5$, $R^6$ and $R^7$ is hydrogen. In another embodiment, the bond between $C_9$ and $C_{10}$ is a double bond, and each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen.

In one embodiment, $R^1$ in the compound of formula IIB is leucine (compound B1). In another embodiment, $R^1$ tryptophan (compound B2). The amino acids are conjugated to the jasmonate derivatives by forming an amide bond between the carboxyl group of the jasmonate and the amino group of the amino acid or the terminal amino group of the peptide.

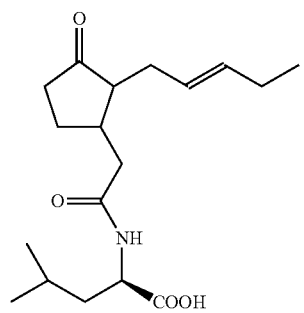

(B1)

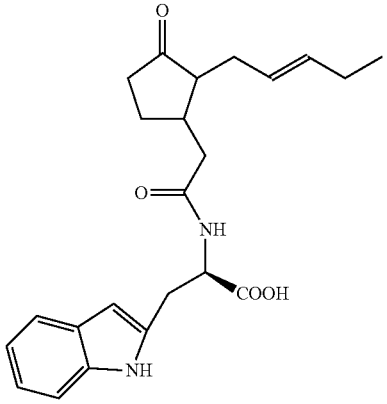

(B2)

Currently preferred compounds of formula IIA or IIB are represented by the structure of formula III.

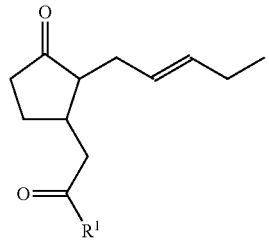

(III)

wherein $R^1$ is as defined above for formula IIA or IIB.

In yet another aspect, the present invention contemplates dimeric, oligomeric or polymeric jasmonate derivatives comprising a plurality of covalently linked jasmonic acid moieties. Without wishing to be bound by any particular mechanism or theory, it is believed that the presence of more than one jasmonic acid moiety in the same molecule may increase the local concentration of the active moiety at the target site, thereby increasing potency of the compound. This concept is exemplified below with respect to jasmonate derivatives represented by the structure of formula IV:

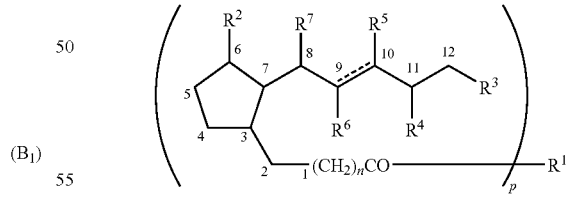

(IV)

wherein
n is independently at each occurrence 0, 1, or 2;
p is 2, 3, 4, 5 or 6;
$R^1$ a linker selected from the group consisting of —O—, polyoxy $C_1$-$C_{12}$ alkylene and a sugar moiety;
$R^2$ is independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can independently at each occurrence be a single or a double bond; and $R^8$, $R^{9a}$ and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

In a currently preferred embodiment, the linker $R^1$ in the compound of formula IV is —O—. In another embodiment, $R^1$ is polyoxy $C_1$-$C_{12}$ alkylene, for example polyethyleneglycol represented by the structure —O(CH$_2$—CH$_2$—O)$_m$— wherein m is an integer of 1 to 20. In yet another embodiment, $R^1$ is a sugar moiety. In yet another embodiment, $R^1$ is a linker selected from the group consisting of —NH—, —S—, —OR$^{10-}$, —NHR$^{11}$—, —SR$^{12}$—, unsubstituted or substituted $C_1$-$C_{12}$ alkylene, polyoxy $C_1$-$C_{12}$ alkylene, polyamino $C_1$-$C_{12}$ alkylene and polythio $C_1$-$C_{12}$ alkylene; wherein $R^{10}$, $R^{11}$ and $R^{12}$ are each independently unsubstituted or substituted $C_1$-$C_{12}$ alkylene. The number of jasmonate units in formula IV (represented by the integer p) depends on the valency of the linker, and is generally selected from the group consisting of 2, 3, 4, 5 and 6.

In another currently preferred embodiment, $R^2$ in the compound of formula IV is oxo. In another currently preferred embodiment, each of $R^3$, $R^4$, $R^5$, $R^6$ and $R^7$ is hydrogen. In another embodiment, the bond between $C_9$ and $C_{10}$ is a double bond, and each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen.

Currently preferred compounds of formula IV are dimeric compounds represented by the structure of formula V:

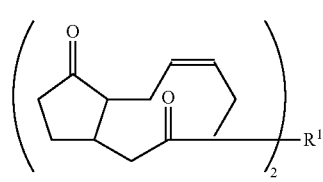
(V)

wherein $R^1$ is as defined above for formula IV.

Specific examples of the compounds of the formula V include but are not limited to compounds C1 and C2.

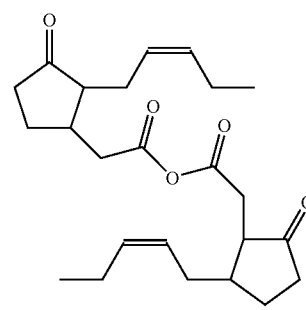
$C_1$

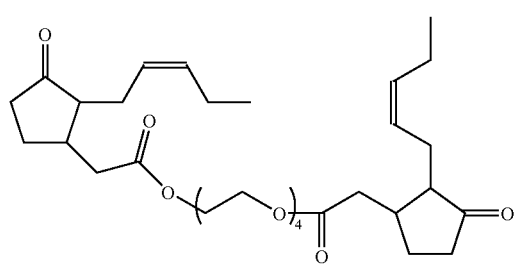
$C_2$

Other currently preferred compounds of formula IV are oligomeric compounds comprising a plurality of jasmonate moieties linked via a linker. In one embodiment, the linker is a sugar moiety, wherein the jasmonate derivatives are bonded to the hydroxyl groups of the sugar. Such oligomeric moieties are represented by the structure of formula (VI):

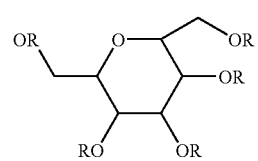
(VI)

wherein
R is represented by the formula:

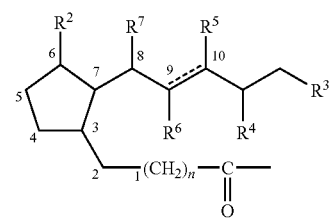

wherein each of $R^2$, $R^3$, $R^4$, $R^5$, $R^6$ and $R^7$ is as defined above.

A specific example of the compounds of the formula VI is a compound of formula C3:

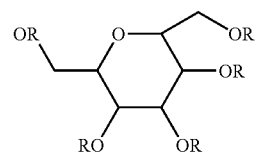
C3

-continued

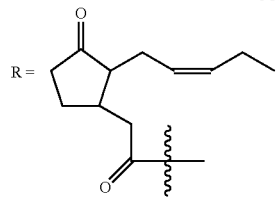

The present invention also contemplates pharmaceutical compositions that include a pharmaceutically acceptable carrier and, as an active ingredient, one or more of the compounds of the invention, represented by any of formulas I, IIA, IIB, III, IV, V or VI, as described above. Preferred compositions have as an active ingredient any one or more of the compounds represented by the structure A1, A2, A3, A4, A5, A6, B1, B2, B3, C1, C2 or C3.

The pharmaceutical compositions of the present invention can be provided in any form known in the art, for example in a form suitable for oral administration (e.g., a solution, a suspension, a syrup, an emulsion, a dispersion, a suspension, a tablet, a pill, a capsule, a pellet, granules and a powder), for parenteral administration (e.g., intravenous, intramuscular, intraarterial, transdermal, subcutaneous or intraperitoneal), for topical administration (e.g., an ointment, a gel, a cream), for administration by inhalation or for administration via suppository. Preferably, in the pharmaceutical composition of the present invention, the active ingredient is dissolved in any acceptable lipid carrier.

Further, in accordance with a preferred embodiment of the present invention, the jasmonate derivatives are administered together with at least one other chemotherapeutic agent. The jasmonate derivative and the at least other chemotherapeutic agent can be administered simultaneously (in the same dosage form or in separate dosage forms), or they can be administered sequentially, in any order.

The present invention additionally provides a method for inhibiting cancer cell proliferation, comprising contacting the cancer cells with a therapeutically effective amount of a compound of any of formulas I, IIA, IIB, III, IV, V or VI, as described herein. Preferably, the compound is one or more of the compounds represented by the structure A1, A2, A3, A4, A5, A6, B1, B2, B2, B3, C1, C2 or C3. In some embodiments, the compound is administered in a pharmaceutical composition.

Furthermore, the present invention provides a method for the treatment of cancer in a subject, by administering to the subject a therapeutically effective amount of the compound of the invention, as described herein. Preferably, the compound is one or more of the compounds represented by the structure A1, A2, A3, A4, A5, A6, B1, B2, B2, B3, C1, C2 or C3. In some embodiments, the compound is administered in a pharmaceutical composition. In one embodiment, the subject is a mammal, preferably a human.

Furthermore, the present invention relates to the use of a compound of any of formulas I, IIA, IIB, III, IV, V or VI according to the present invention in the preparation of a medicament useful for the treatment of cancer.

The compounds of the present invention are active against a wide range of cancers, including carcinomas, sarcomas, myelomas, leukemias, lymphomas and mixed type tumors. Particular categories of tumors amenable to treatment include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer to be treated is selected from the group consisting of prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer. According to exemplary embodiments, the cancer to be treated is selected from breast cancer, kidney cancer, stomach cancer, leukemia, including lymphoblastic leukemia, lung carcinoma, melanoma and colon cancer.

The jasmonate derivatives of the present invention are significantly more potent than the compounds disclosed in U.S. Pat. No. 6,469,061 and WO 2005/054172. They display an unexpected cyclotoxic effect with a high degree of specificity towards malignant cells.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1: shows the cytotoxic activity of increasing concentrations (0.01-1 mM) of several compounds of the invention in a lymphoblastic leukemia cell line (Molt-4). Cytotoxicity (%) is plotted against the compound concentration.

DETAILED DESCRIPTION OF THE PRESENT INVENTION

Figure 1A:
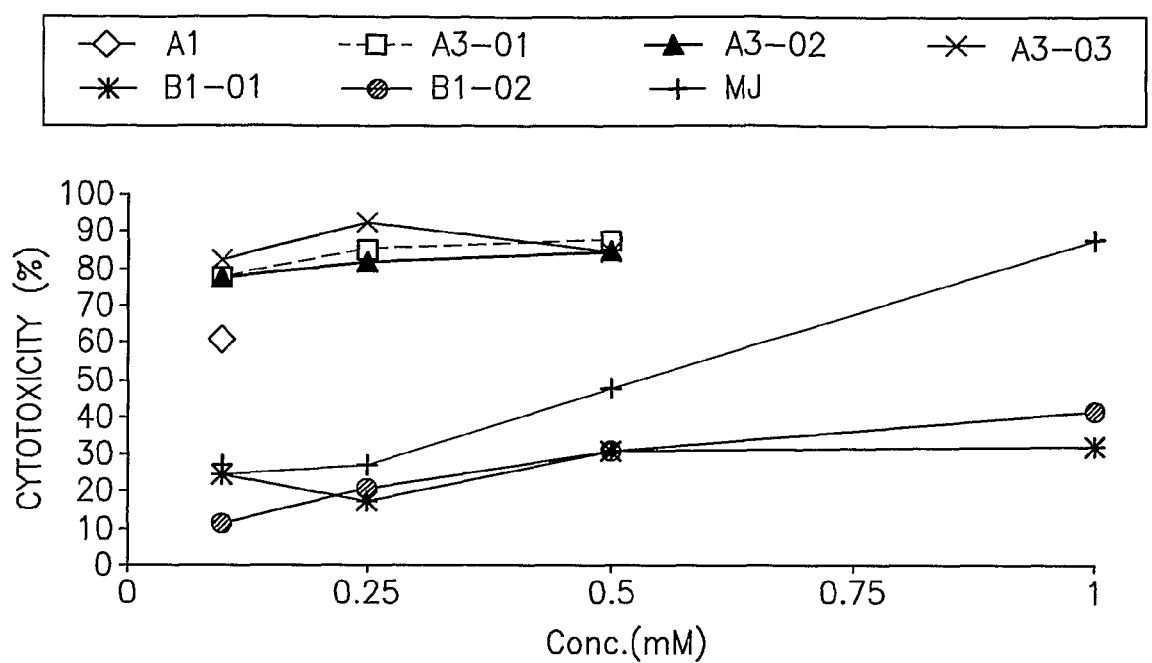
FIG. 1A shows results for compounds A1, A3 and B1.

The present invention relates to novel jasmonate derivative compounds. Preferred jasmonate derivatives are thiazole derivatives represented by the structure of formula I. Other preferred jasmonate derivatives are compounds represented by the structure of formula IIA. Other preferred jasmonate derivatives are amino acid-jasmonate conjugates represented by the structure of formula IIB. Still other preferred jasmonate derivatives are jasmonate oligomers represented by the structure of formulas IV, V or VI. Some of these compounds are significantly more potent than the compounds disclosed in the art, and exert selective cytotoxicity on cancerous cells, e.g. lymphocytes, carcinoma cells and breast cancer cells, while having very low effect on normal cells. As such, the compounds of the present invention are useful in inhibiting cancer cell proliferation and treating a variety of cancers.

In one embodiment, the compounds of the present invention are heterocyclic jasmonate derivatives represented by the general structure of formula I:

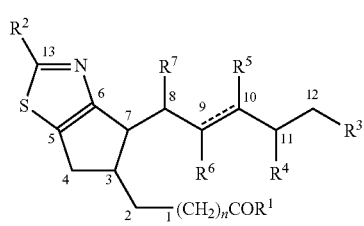

wherein n is 0, 1, or 2;

$R^1$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, a natural or unnatural amino acid, a peptide, $OR^8$ and $NR^{9a}R^{9b}$;

$R^2$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, $NR^{9a}R^{9b}$, $NHCOR^{10}$ and $NHSO_2R^{11}$;

$R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can be a single or a double bond; and $R^8$, $R^{9a}$, $R^{9b}$, $R^{10}$ and $R^{11}$, are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

In one currently preferred embodiment, $R^1$ in formula I is hydroxyl. In another embodiment, $R^1$ is alkyloxy, e.g., methoxy. In another embodiment, $R^1$ is O-glucosyl. In yet another embodiment, $R^1$ is $NR^{9a}R^{9b}$, wherein $R^{9a}$ and $R^{9b}$ are as described in Formula (I) above. In another embodiment, $R^1$ is $NR^{9a}R^{9b}$ wherein $R^{9a}$ is hydrogen and $R^{9b}$ is selected from the group consisting of unsubstituted or substituted $C_1$-$C_{12}$ alkyl, unsubstituted or substituted $C_3$-$C_8$ cycloalkyl, unsubstituted or substituted aryl, and unsubstituted or substituted heteroaryl. The substituent on the alkyl, cycloalkyl, aryl or heteroaryl can be any one or more of the substituents described herein.

In another embodiment, $R^{9a}$ and $R^{9b}$ together with the nitrogen to which they are attached form an unsubstituted or substituted heterocyclic or heteroaromatic ring optionally containing one or more additional heteroatom selected from O, N and S. The heterocyclic ring can be saturated or unsaturated, and can be any one or more of the heterocyclic rings described herein. Non-limiting examples of such rings include piperidinyl and piperazinyl, which can be unsubstituted or substituted with any one or more of the substituents described herein.

In one currently preferred embodiment, $R^2$ in Formula I is $NR^{9a}R^{9b}$ wherein $R^{9a}$ and $R^{9b}$ are as described in Formula I above. In another embodiment, $R^2$ is $NHCOR^{10}$ wherein $R^{10}$ is as described in Formula I above. In yet another embodiment, $R^2$ is $NHSO_2R^{11}$, wherein $R^{11}$ is as described in Formula I above. In one currently preferred embodiment, $R^2$ is phenyl. In another currently preferred embodiment, $R^2$ is $NHCOR^{10}$ wherein $R^{10}$ is a $C_1$-$C_{12}$ alkyl substituted with an aryl or heteroaryl (e.g., methylenethiophene). In another currently preferred embodiment, $R^2$ is $NHSO_2R^{11}$ wherein $R^{11}$ is aryl or heteroaryl. In yet another preferred embodiment $R^2$ is $NH_2$. In yet another preferred embodiment, $R^2$ is NH-phenyl.

In one currently preferred embodiment, the bond between $C_9$ and $C_{10}$ is a double bond. In another currently preferred embodiment, the bond between $C_9$ and $C_{10}$ is a single bond. In another embodiment, each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen. In yet another embodiment, the bond between $C_9$ and $C_{10}$ is a double bond, and each of $R^3$, $R^4$, $R^5$, $R^6$ and $R^7$ is hydrogen.

Specific examples of the compounds of the present invention include but are not limited to:

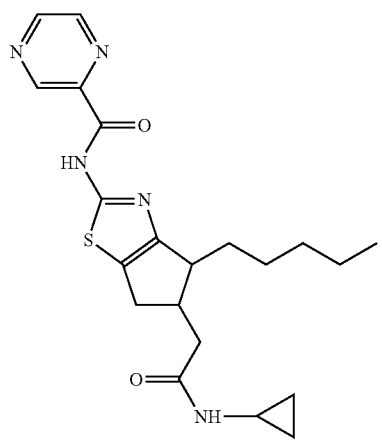

$A_1$

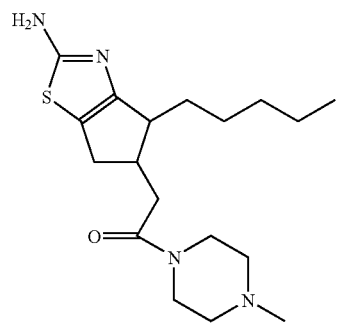

$A_2$

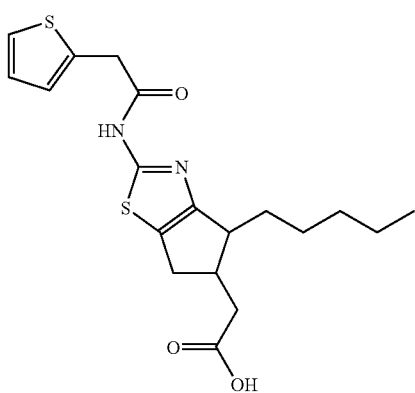

$A_3$

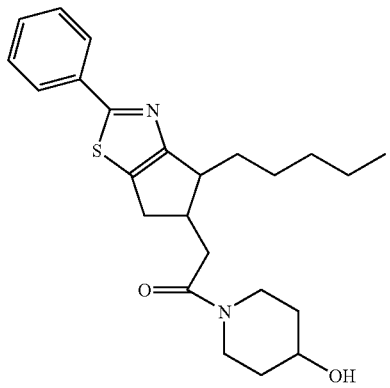

$A_4$

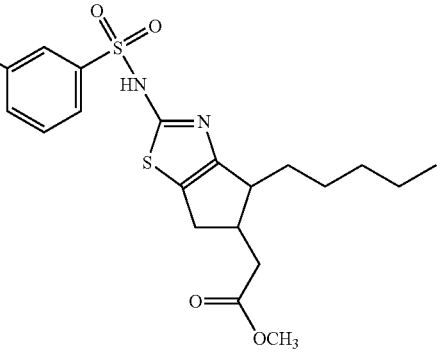

$A_5$ and

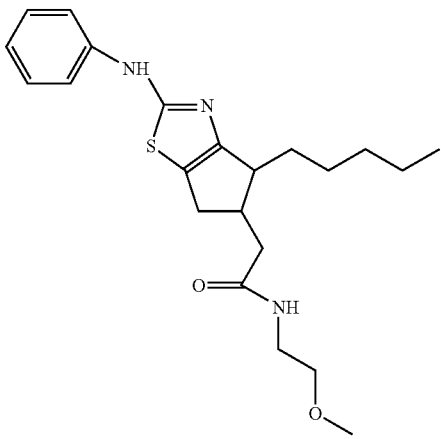

$A_6$

In another aspect, the present invention relates to jasmonate derivatives represented by the structure of formula IIA.

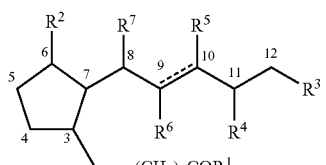

(IIA)

wherein n is independently at each occurrence 0, 1, or 2;

$R^1$ is a group of the formula:

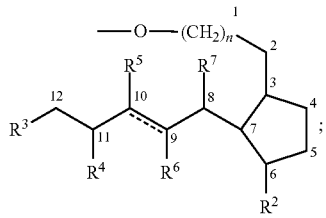

$R^2$ is independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can independently at each occurrence be a single or a double bond; and $R^8$, $R^{9a}$ and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S; including salts, hydrates, solvates, polymorphs, optical isomers, geometrical isomers, enantiomers, diastereomers, and mixtures thereof.

In one embodiment, $R^1$ in the compound of formula IIA is a group of the formula:

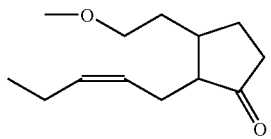

In a currently preferred embodiment, $R^2$ in the compound of formula IIA is oxo. In another currently preferred embodiment, each of $R^3$, $R^4$, $R^5$, $R^6$ and $R^7$ is hydrogen. In another embodiment, the bond between $C_9$ and $C_{10}$ is a double bond, and each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen.

A specific example of the compounds of the formula IIA is a compound of formula B3:

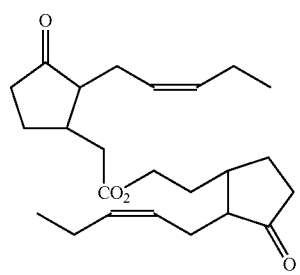

In another embodiment, the present invention relates to jasmonate-amino acid or jasmonate-peptide conjugates represented by the structure of formula IIB:

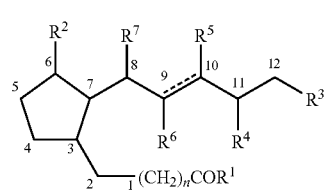

(IIB)

wherein n is 0, 1, or 2;

$R^1$ is a natural or unnatural amino acid or a peptide;

$R^1$ is selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;

$R^3$, $R^4$, $R^5$, $R^6$ and $R^7$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can be a single or a double bond; and $R^8$, $R^{9a}$ and $R^{9b}$ are each independently selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, polymorphs, optical isomers, geometrical isomers, enantiomers, diastereomers, and mixtures thereof.

In a currently preferred embodiment, $R^2$ in the compound of formula IIB is oxo. In one currently preferred embodiment, the bond between $C_9$ and $C_{10}$ is a double bond. In another currently preferred embodiment, the bond between $C_9$ and $C_{10}$ is a single bond. In another embodiment, each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen. In yet another embodiment, the bond between $C_9$ and $C_{10}$ is a double bond, and each of $R^3$, $R^4$, $R^5$, $R^6$ and $R^7$ is hydrogen.

In another currently preferred embodiment, $R^1$ is a residue of tryptophan. In another currently preferred embodiment, $R^1$ is a residue of leucine.

In one embodiment, the amino acids or peptides are conjugated to the jasmonate derivatives by forming an amide bond between the carboxyl group of the jasmonate and the amino group of the amino acid or the terminal amino group of the peptide. Exemplary compounds in which $R^1$ in the compound of formula IIB is leucine (compound B1) or tryptophan (compound B2) are shown below (B1)

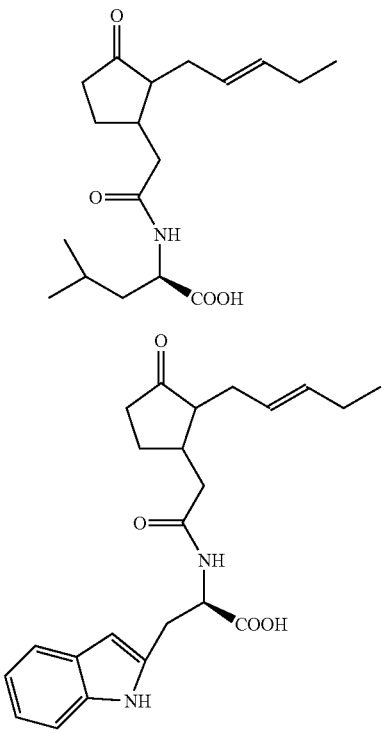

(B2)

Alternatively, in another embodiment, the amino acids or peptides are conjugated to the jasmonate derivatives by a forming bond between the carboxyl group of the jasmonate and a side chain of the amino acid, or a side chain of an amino acid in the peptide chain. In this way, ester, amide or thioester bonds are formed through available heteroatoms in the side chains such as O, N or S, respectively. Alternatively, the bond can be formed between the jasmonate derivative and a carboxyl group in the amino acid or peptide (either the alpha carboxyl group or a carboxylic acid group in the side chain). It should be apparent to a person of skill in the art that any other methods for coupling the amino acids or peptides to the jasmonate derivatives, known to a person of skill in the art, are also contemplated by the present invention.

Currently preferred compounds of formula IIA or IIB are represented by the structure of formula III:

(III)

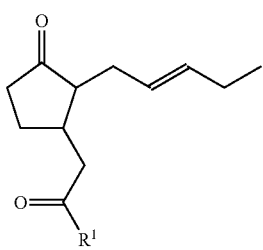

wherein $R^1$ is as defined above for formula IIA or formula IIB.

In yet another embodiment the present invention relates to oligomeric jasmonate derivatives, represented by the structure of formula IV:

(IV)

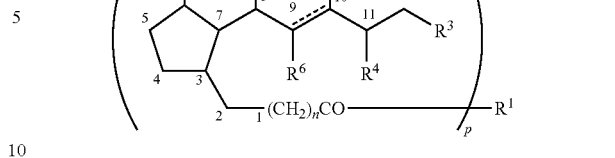

wherein
n is independently at each occurrence 0, 1, or 2;
p is 2, 3, 4, 5 or 6;
$R^1$ a linker selected from the group consisting of —O—, polyoxy $C_1$-$C_{12}$ alkylene and a sugar moiety;
$R^2$ is independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$, oxo and $NR^{9a}R^{9b}$;
$R^3$, $R^4$, $R^5$, $R^6$ and $R^7$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;
wherein the bond between $C_9$ and $C_{10}$ can independently at each occurrence be a single or a double bond; and
$R^8$, $R^9$, and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;
including salts, hydrates, solvates, polymorphs, optical isomers, geometrical isomers, enantiomers, diastereomers, and mixtures thereof.

In a currently preferred embodiment, $R^1$ in the compound of formula IV is —O—. In another embodiment, $R^1$ is polyoxy $C_1$-$C_{12}$ alkylene, for example polyethyleneglycol represented by the structure —O(CH$_2$—CH$_2$—O)$_m$, wherein m is an integer of 1 to 20. In yet another embodiment, $R^1$ is a sugar moiety. However, the use of other linkers are contemplated by the present invention. For example, in some embodiments, $R^1$ is a linker selected from the group consisting of —NH—, —S—, —$OR^{10}$—, —$NHR^{11}$—, —$SR^{12}$—, unsubstituted or substituted $C_1$-$C_{12}$ alkylene, polyamino $C_1$-$C_2$ alkylene and polythio $C_1$-$C_{12}$ alkylene; wherein $R^{10}$, $R^{11}$ and $R^{12}$ are each independently unsubstituted or substituted $C_1$-$C_{12}$ alkylene.

In another currently preferred embodiment, $R^2$ in the compound of formula IV is oxo. In one currently preferred embodiment, the bond between $C_9$ and $C_{10}$ is a double bond. In another currently preferred embodiment, the bond between $C_9$ and $C_{10}$ is a single bond. In another embodiment, each of $R^3$, $R^4$, $R^5$, $R^6$ and $R^7$ is hydrogen. In yet another embodiment, the bond between $C_9$ and $C_{10}$ is a single bond, and each of $R^3$, $R^4$, $R^5$, $R^6$ and $R^7$ is hydrogen. In yet another embodiment, the bond between $C_9$ and $C_{10}$ is a double bond, and each of $R^3$, $R^4$, $R^5$, $R^6$ and $R^7$ is hydrogen.

It is to be understood that the number of jasmonate units in the oligomeric compounds of formula IV (designated by the integer "p") will depend on the nature of the linker. For example, for bivalent linkers such as —O— or polyoxy $C_1$-$C_{12}$ alkylene, there will be two jasmonate moieties (i.e., p=2), thus defining dimeric compounds. Examples of such dimeric compounds of formula IV are represented by the structure of formula V:

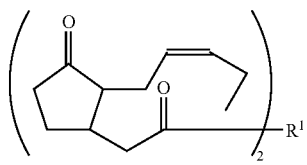
(V)

wherein $R^1$ is as defined above.

Specific examples of dimeric compounds of the formula IV include but are not limited to compounds C1 and C2.

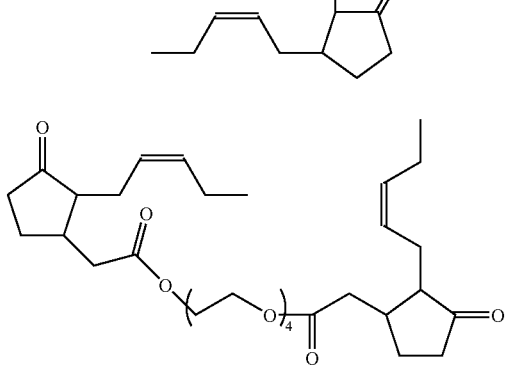
C1
C2

In addition to dimers, the present invention further contemplates the use of oligomeric compounds formed by using multivalent linkers, for example sugar moieties. In this case, the number of jasmonate units in the oligomer will depend on the number of available sites on the linker. For example, in one currently preferred embodiment, the linker is a sugar moiety comprising 2, 3, 4 or 5 hydroxyl groups that are available to bond to jasmonate units. This concept is exemplified below with respect to jasmonate-sugar derivatives, represented by the structure of formula VI:

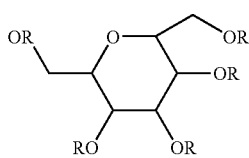
(VI)

wherein
R is represented by the formula:

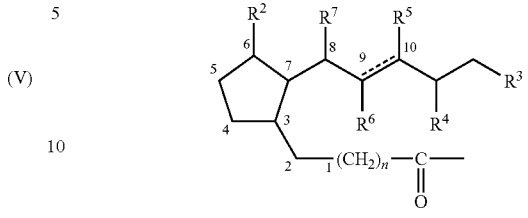

wherein each of $R^2$, $R^3$, $R^4$, $R^5$, $R^6$ and $R^7$ is as defined above.

Specific examples of the compounds of the formula VI includes is not limited to compound $C_3$:

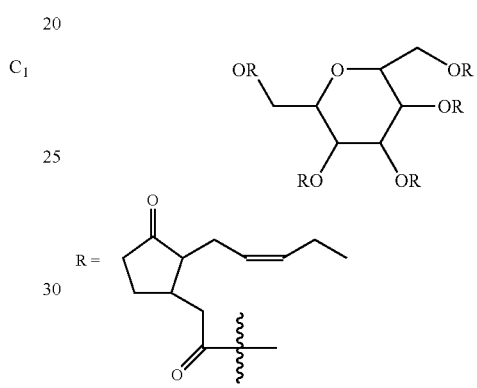
C3

It is apparent to a person of skill in the art that any sugar derivative can be used as a linker for the multimeric compounds of formula VI, for example glucose. It is further apparent to a person of skill in the art, that the sugar moiety in the multimeric jasmonate derivatives is not limited to the pyranoside ring of formula VI above. Rather, derivatives based on any sugar pyranoside or furanoxide are also contemplated, for example aldohexose such as allose, altrose, glucose, mannose, gulose, idose, galactose and talose; aldoketoses such as psiocose, fructose, sorbose and tatasose; aldopentoses such as ribose, arabinose, xylose and lyxose; and the like. The use of D sugars as well as L sugars is contemplated.

Still further, any other linker based on any polyfunctional group such as a polyalcohol, polyamine, polycarboxylic acid and the like, can be used to prepare the multimeric compounds of the present invention.

These compounds can be prepared as salts or encapsulated in a carrier to aid in their solubility.

Chemical Definitions

The term "$C_1$ to $C_{12}$ alkyl" used herein alone or as part of another group denotes linear and branched, saturated or unsaturated (e.g, alkenyl, alkynyl) groups, the latter only when the number of carbon atoms in the alkyl chain is greater than or equal to two, and can contain mixed structures. Preferred are alkyl groups containing from 1 to 4 carbon atoms ($C_1$ to $C_4$ alkyls). Examples of saturated alkyl groups include but are not limited to methyl, ethyl, n-propyl, isopropyl, n-butyl, iso-butyl, sec-butyl, tert-butyl, amyl, tert-amyl, hexyl, heptyl, octyl, nonyl, decyl, undecyl, dodecyl and the like. Examples of alkenyl groups include vinyl, allyl, butenyl and the like. Examples of alkynyl groups include ethynyl, propynyl and the like. Similarly, the term "$C_1$ to $C_{12}$ alkylene" denotes a bivalent radicals of 1 to 12 carbons.

The $C_1$ to $C_{12}$ alkyl group can be unsubstituted, or substituted with one or more substituents selected from the group consisting of The term halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio arylthio, or $C_1$ to $C_{10}$ alkylsulfonyl groups. Any substituent can be unsubstituted or further substituted with any one of these aforementioned substituents.

The term "$C_3$ to $C_8$ cycloalkyl" used herein alone or as part of another group denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzo-heterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The term "halogen" or "halo" as used herein alone or as part of another group refers to chlorine, bromine, fluorine, and iodine.

The term "amino" as used herein alone or as part of another group refers to an $NH_2$ group. The terms "alkyl amino, dialkylamino, arylamino, diaryl amino, heteroarylamino, diheteroarylamino" and variants thereof as used herein refer to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl and the like. These substituents can be further substituted with any one or more of the substituents defined above for alkyl. In addition, the amino substituents (e.g., $NR^{9a}R^{9b}$) can together with the nitrogen atom to which they are attached form a heterocyclic ring which can be any one of the heterocyclic rings defined above.

The term "hydroxy" refers to an OH group. The terms "alkoxy", "aryloxy" "arylalkyloxy" or "heteroaryloxy" as used herein alone or as part of another group includes any of the above alkyl, aryl or heteroaryl groups linked to an oxygen atom. Nonlimiting examples of an alkoxy group is methoxy, ethoxy, n-propoxy, isopropoxy, n-butoxy, t-butoxy and like groups. An example of an aryloxy group is phenyloxy (phenoxy). The alkoxy, aryloxy, arylalkyloxy or heteroaryloxy groups can be unsubstituted or substituted with any one or more of the substituents defined above for alkyl.

The term "carboxy" as used herein alone or as part of another group refers to a COO group, and further encompasses carboxylate salts thereof of the formula COOM wherein M is a metal ion. The term "metal ion" refers to alkali metal ions such as sodium, potassium or lithium and alkaline earth metal ions such as magnesium and calcium, as well as zinc and aluminum.

The term "acyl" encompasses groups such as formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Preferred acyl groups are acetyl and benzoyl.

The term "thio" as used herein alone or as part of another group refers to an SH group. The terms "alkylthio", "arylthio" or "arylalkylthio" as used herein alone or as part of another group refer to any of the above alkyl, arylalkyl or aryl groups linked to a sulfur atom.

The term "sulfonyl" as used herein alone or as part of another group refers to —S(O)$_2$—. The term "sulfonylamino" as used herein alone or as part of another group refers to —S(O)$_2$—NH. The term "sulfinyl" refers to —S(O)—. The term "sulfinylamino" as used herein alone or as part of another group refers to —S(O)—NH. The term "oxo" as used herein alone or as part of another group refers to —O—. The term "cyano" as used herein alone or as part of another group refers to a CN group. The term "nitro" as used herein alone or as part of another group refers to an $NO_2$ group.

The term "polyoxy $C_1$-$C_{12}$ alkylene" as used herein alone or as part of another group refers to two or more units of oxy $C_1$-$C_{12}$ alkylene (i.e., a $C_1$-$C_{12}$ alkylene moiety as defined above bonded to an oxygen), for example a compound represented by the structure —O[(CH$_2$)$_p$O)]$_m$— wherein m is an integer of 1 to 20 and p is an integer of 1 to 12. An example of a polyoxy $C_1$-$C_{12}$ alkylene group is polyethylene glycol represented by the structure —O(CH$_2$—CH$_2$—O)$_m$.

Similarly, the term "polyamino $C_1$-$C_{12}$ alkylene" as used herein alone or as part of another group refers to two or more units of amino $C_1$-$C_{12}$ alkylene (i.e., a $C_1$-$C_{12}$ alkylene moiety as defined above bonded to an NH), for example a compound represented by the structure —NH[(CH$_2$)$_p$NH)]$_m$— wherein m is an integer of 1 to 20 and p is an integer of 1 to 12. An example of a polyamino $C_1$-$C_{12}$ alkylene group is polyethylenediamine represented by the structure —NH(CH$_2$—CH$_2$—NH)$_m$.

Similarly, the term "polythio $C_1$-$C_{12}$ alkylene" as used herein alone or as part of another group refers to two or more units of thio $C_1$-$C_{12}$ alkylene (i.e., a $C_1$-$C_{12}$ alkylene moiety as defined above bonded to a sulfur), for example a compound represented by the structure —S[(CH$_2$)$_p$S)]$_m$— wherein m is an integer of 1 to 20 and p is an integer of 1 to 12. An example of a polythio $C_1$-$C_{12}$ alkylene group is represented by the structure —S(CH$_2$—CH$_2$—S)$_m$.

The terms "natural and unnatural amino acids" (α-amino acid) refers to both the naturally occurring amino acids and other unnaturally amino acids including both optically active (D and L) forms as well as racemic derivatives. As contemplated herein, the amino acids are conjugated to the jasmonate derivatives by forming an amide bond between the carboxyl group of the jasmonate and the amino group of the amino acid. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of unnatural α-amino acids include N-methyl-alanine, α-aminoisobutyric acid, α-aminobutyric acid, γ-aminobutyric acid, citrulline, N-methyl-glycine, N-methyl-glutamic acid, homocitrulline, homoproline, homoserine, hydroxyproline, norleucine, 4-aminophenylalanine, statine, hydroxylysine, kynurenine, 3-(2'-naphthyl)alanine, 3-(1'-naphthyl)alanine, methionine sulfone, (t-butyl)alanine, (t-butyl)glycine, 4-hydroxyphenylglycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxykynurenine, 3-aminotyrosine, trifluoromethyl-alanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentanecarboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, elastatinal, norleucine, norvaline, alloisoleucine, homoarginine, thioproline, dehydroproline, hydroxyproline, homoproline, α-amino-n-butyric acid, cyclohexylalanine, 2-amino-3-phenylbutyric acid, β-2- and 3-thienylalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-(sulfo)tyrosine, 3-(carboxy)tyrosine, 3-(phospho)tyrosine, the 4-methane sulfonic acid ester of tyrosine, 4-methane phosphonic acid ester of tyrosine, 3,5-diiodotyrosine, 3-nitrotyrosine, ε-alkyl lysine, and δ-alkyl ornithine.

Two or more of the aforementioned amino acids can be linked via amide bonds to form peptides of various lengths. Peptides comprising two or more natural or unnatural amino acids can also be incorporated in the jasmonate derivatives of the present invention.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R, S or d, D, l, L or d, l, D, L. Compounds comprising amino acid residues include residues of D-amino acids, L-amino acids, or racemic derivatives of amino acids. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1-19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group are also contemplated.

The present invention also includes solvates of compounds I, II, III, IV and V and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of compounds I, II, III, IV and V and salts thereof. The term "polymorph" refers to a particular crystalline state of a substance, which can be characterized by particular physical properties such as X-ray diffraction, IR spectra, melting point, and the like.

Therapeutic Use

As described herein, the compounds of the present invention are potent cytotoxic agents that are capable of inhibiting cancer cell proliferation in a wide variety of cancer cells. The present invention thus provides powerful methods to the chemoprevention and treatment of cancer that have not been previously described.

Thus, in one aspect the present invention additionally provides a method for inhibiting cancer cell proliferation, comprising contacting the cancer cells with a therapeutically effective amount of a compound of the present invention, as described herein. Preferably, the compound is one or more of the compounds represented by the structure A1, A2, A3, A4, A5, A6, B1, B2, B3, C1, C2 and C3. In some embodiments, the compound is administered in a pharmaceutical composition.

Furthermore, the present invention provides a method for the treatment of cancer in a subject, by administering to the subject a therapeutically effective amount of the compound of the invention, as described herein. Preferably, the compound is one or more of the compounds represented by the structure A1, A2, A3, A4, A5, A6, B1, B2, B3, C1, C2 and C3. In some embodiments, the compound is administered in a pharmaceutical composition. In one embodiment, the subject is a mammal, preferably a human. However, the present invention also contemplates using the compounds of the present invention for non-mammal humans, e.g., in veterinary medicine.

Furthermore, the present invention relates to the use of a compound of formula I, IIA, IIB, III, IV, V or VI according to the present invention in the preparation of a medicament useful for the treatment of cancer.

It is to be understood that whenever the terms "treating or inhibiting a malignant cell proliferative disease or disorder", "treating or inhibiting a non-solid cancer", "treating or inhibiting a tumor" are used herein in the description and in the claims, they are intended to encompass tumor formation, primary tumors, tumor progression or tumor metastasis.

The term "inhibition of proliferation" in relation to cancer cells, in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. This term also encompasses prevention for prophylactic situations or for those individuals who are susceptible to contracting a tumor. The administration of the compounds of the present invention will reduce the likelihood of the individual contracting the disease. In preferred situations, the individual to whom the compound is administered does not contract the disease.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

A "therapeutic" treatment is a treatment administered to a subject who exhibits signs of pathology for the purpose of diminishing or eliminating those signs. A "therapeutically effective amount" of a compound of the invention is that amount of compound which is sufficient to provide a beneficial effect to the subject to which the compound is administered.

Cancers may be classified in two ways: by the type of tissue in which the cancer originates (histological type) and by primary site, or the location in the body where the cancer first developed. The international standard for the classification and nomenclature of histologies is the International Classification of Diseases for Oncology, Third Edition.

From a histological standpoint there are hundreds of different cancers, which are grouped into five major categories: carcinoma, sarcoma, myeloma, leukemia, and lymphoma. In addition, there are also some cancers of mixed types.

Carcinoma refers to a malignant neoplasm of epithelial origin or cancer of the internal or external lining of the body. Carcinomas, malignancies of epithelial tissue, account for 80 to 90 percent of all cancer cases. Epithelial tissue is found throughout the body. It is present in the skin, as well as the covering and lining of organs and internal passageways, such as the gastrointestinal tract.

Carcinomas are divided into two major subtypes: adenocarcinoma, which develops in an organ or gland, and squamous cell carcinoma, which originates in the squamous epithelium. Most carcinomas affect organs or glands capable of secretion, such as the breasts, which produce milk, or the lungs, which secrete mucus, or colon or prostate or bladder.

Adenocarcinomas generally occur in mucus membranes and are first seen as a thickened plaque-like white mucosa. They often spread easily through the soft tissue where they occur. Squamous cell carcinomas occur in many areas of the body.

Sarcoma refers to cancer that originates in supportive and connective tissues such as bones, tendons, cartilage, muscle, and fat. Generally occurring in young adults, the most common sarcoma often develops as a painful mass on the bone. Sarcoma tumors usually resemble the tissue in which they grow.

Examples of sarcomas are: Osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); Mesenchymous or mixed mesodermal tumor (mixed connective tissue types);

Myeloma is cancer that originates in the plasma cells of bone marrow. The plasma cells produce some of the proteins found in blood.

Leukemias ("non-solid tumors" or "blood cancers") are cancers of the bone marrow (the site of blood cell production). The disease is often associated with the overproduction of immature white blood cells. Leukemia also affects red blood cells and can cause poor blood clotting and fatigue due to anemia. Examples of leukemia include: Myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); Polycythemia vera or erythremia (malignancy of various blood cell products, but with red cells predominating)

Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias, which are sometimes called "non-solid tumors," lymphomas are "solid cancers." Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma.

Mixed Type cancers contain several types of cells. The type components may be within one category or from different categories. Some examples are: adenosquamous carcinoma; mixed mesodermal tumor; carcinosarcoma; teratocarcinoma As used herein, the term "cancer" includes the above categories of carcinoma, sarcoma, mycloma, leukemia, lymphoma and mixed type tumors. In particular, the term cancer includes: lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

More preferably, the cancer is selected from the group consisting of prostate cancer, breast cancer, skin cancer, colon cancer, lung cancer, pancreatic cancer, lymphoma, myeloma, leukemia, head and neck cancer, kidney cancer, stomach cancer, ovarian cancer, bone cancer, liver cancer or thyroid cancer. Even more preferably, the cancer is selected from leukemia, including lymphoblastic leukemia, lung carcinoma, melanoma, kidney cancer, stomach cancer and colon cancer.

In other embodiments of the use of preparing a medicament, the medicament additionally comprises at least one active chemotherapeutic agent other than the compounds of the invention. In certain embodiments, the compounds of the invention may be administered alongside with at least one traditional chemotherapeutic drug that is effective at treating the particular cancer. The administration can be concurrent (either combined in one dosage form or in separate dosage forms) or sequential. If provided sequentially, the jasmonate derivative can be administered before or after treatment with the additional chemotherapeutic agent(s). The combination of a compound of the invention and the traditional drug may allow administration of a lower dosage of the traditional drug, and thus the side effects experienced by the subject may be significantly lower, while a sufficient chemotherapeutic effect is nevertheless achieved.

Pharmaceutical Compositions

Although the heterocyclic jasmonate derivatives of the present invention can be administered alone, it is contemplated that these compounds will be administered in a pharmaceutical composition containing the jasmonate derivative together with a pharmaceutically acceptable carrier or excipient.

Preferably, in the pharmaceutical composition the active ingredient is dissolved in any acceptable lipid carrier (e.g., fatty acids, oils to form, for example, a micelle or a liposome). Lipid carrier include, for example, phospholipids (e.g., lecithin).

Further, in accordance with a preferred embodiment of the present invention, the composition additionally comprises at least one other chemotherapeutic agent The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, via a suppository or via dialysis. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Other pharmaceutical carriers can be sterile liquids, such as water, alcohols (e.g., ethanol) and lipid carriers such as oils, (including those of petroleum, animal, vegetable or synthetic origin, such as peanut oil, soybean oil, mineral oil, sesame oil and the like), phospholipids (e.g. lecithin), polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

The formulations can additionally include lubricating agents such as talc, magnesium stearate, and mineral oil; wetting agents, anti-oxidants, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Fatty acids can also be included.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, alcoholic solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols.

Alternative formulations include nasal sprays, liposomal formulations, slow-release formulations, controlled-release formulations and the like, as are known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some preferred embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In a preferred form, a compound of the invention is administered in combination with a biodegradable, biocompatible polymeric implant, which releases the compound over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intraarterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Alternatively, the jasmonate derivatives of the present invention can be used in hemodialysis such as leukophoresis and other related methods, e.g., blood is drawn from the patient by a variety of methods such dialysis through a column/hollow fiber membrane, cartridge etc, is treated with the jasmonate derivatives Ex-vivo, and returned to the patient following treatment. Such treatment methods are well known and described in the art. See, e.g., Kolho et al. (J. Med. Virol. 1993, 40(4): 318-21); Ting et al. (Transplantation, 1978, 25(1): 31-3); the contents of which are hereby incorporated by reference in their entirety.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, 0.1 mg/kg to 100 mg/kg and even more preferably 1 mg/kg to 10 mg/kg. Effective doses may be extrapolated from dose-response curves derived from in vitro or animal model test bioassays or systems.

A currently preferred pharmaceutical composition for use in the present invention includes at least one jasmonate derivatives, an alcohol (e.g., ethanol), a phospholipids (e.g., lecithin), an anti-oxidant (e.g., Ascorbyl-Palmitate), propylene glycol; and alpha Tocopheryl Polyethylene Glycol In one preferred embodiment, the composition comprises:

about 0.1 to about 50 µg/ml a jasmonate active ingredient, preferably about 5 µg/ml;

about 1-100 µg/ml, ethanol, preferably about 20 µg/ml;

about 1-100 µg/ml, propylene glycol, preferably about 20 µg/ml;

about 1-100 mg/ml, lecithin preferably about 30 mg/ml;

about 0.1-20 mg/ml ascorbyl palmitate, preferably about 1 mg/ml, about 2 mg/ml, about 5 mg/ml or about 10 mg/ml; and about 0.1-20 mg/ml alpha Tocopheryl Polyethylene Glycol, preferably about 0.4 mg/ml or 1 mg/ml.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods

Cytotoxicity Assay Used in Examples

Measurement of reduction in the number of living cells was determined by the CellTiter 96 Aqueous Non-Radioactive Cell Proliferation Assay (XTT Cell Proliferation Kit assay (Biological industries, Beit-Haemek, Israel)). Upon completion of a given experiment, MTS (a tetrazolium compound) at 333 µg/ml+phenazine methosulfate (at 25 µM) was added to each well of the 96-well plate for 1 hour at 37° C. This allowed for development of a color reaction in which dehydrogenases reduce the MTS in metabolically active cells. Soluble MTS formazan product was measured at a wavelength of 490 nm using a CERES 900 HDI ELISA reader (Bio-Tek Instruments, Inc, Highland Park, Vt.).

Percentage of Optical density is directly proportional to the number of living cells in culture. Cytotoxicity (%) was calculated in the following way: [(OD of control cells —OD of drug-treated cells)/OD of control cells]×100.

Example 1

Cytotoxicity of Jasmonate Derivatives A1-A6, B1 and B2 Towards Leukemia Cells

The cytotoxicity of jasmonate derivatives A1-A6, B1 and B2 was compared to that of the previously studied jasmonate, methyl jasmonate (MJ). The cytotoxicity of each compound was determined in Molt-4-Human acute lymphoblastic leukemia cell-line.

Experimental Set Up

Molt-4 lymphoblastic leukemia cells (at $1.5 \times 10^4$/well) were seeded in 96-well plates and jasmonate derivatives were added at concentration ranging from 0.1-1 mM for 24 hours. Each experimental point was performed in triplicates. Untreated cells were used as control. The test compounds were prepared as a stock of 100 mM in DMSO. Dilutions were performed in culture medium and DMSO so that the maximal concentration of DMSO in each well was 0.5%. This concentration of DMSO by itself did not affect the viability of any of the cell lines. Cytotoxicity and optical density were determined as described above.

Results

Figure 1B:
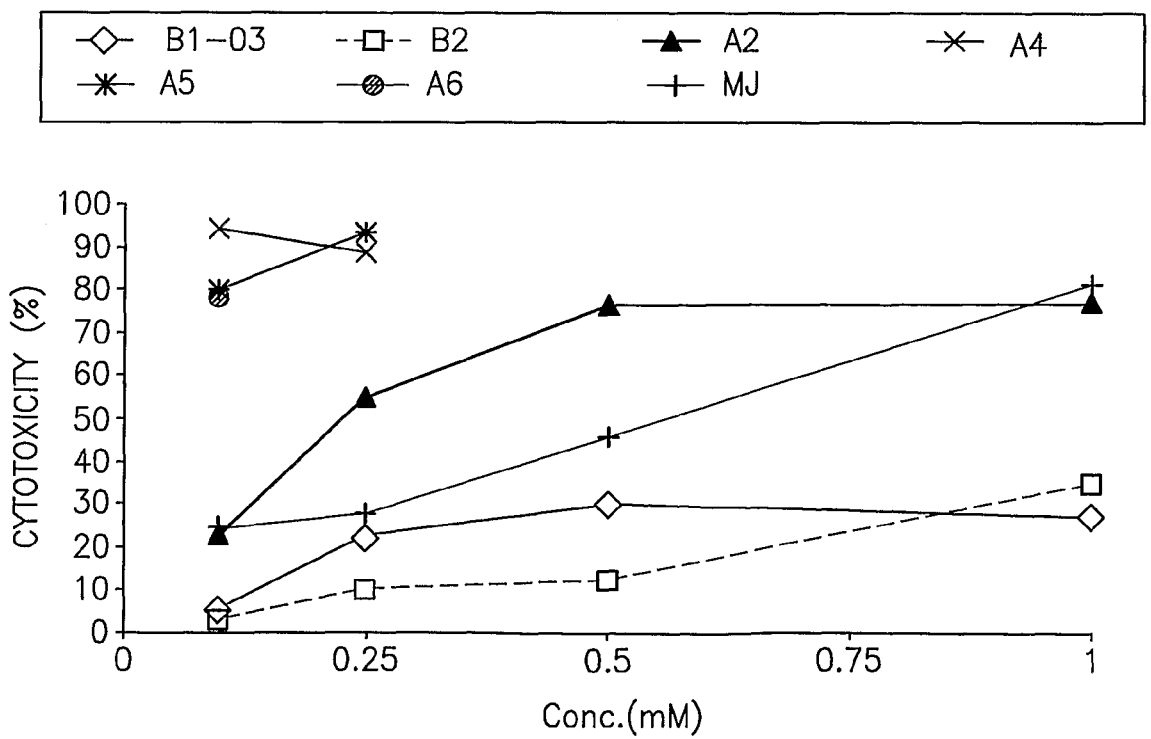
FIG. 1B shows results for compounds A2, A4, A5, A6, B1 and B2. Duplicative experiments for a specific compound are indicated by the suffixes -01, -02, etc. Methyl jasmonate (MJ) is used as a control.

The cytotoxicity of the novel derivatives was compared to that of methyl jasmonate. A first screening performed at concentrations of 0.1-1 mM determined that several compounds were more potent than methyl jasmonate (see FIGS. 1A and 1B—compounds A1, A2, A3, A4, A5 and A6), and several compounds were very potent even at a concentration of 0.1 mM (Compounds A1, A3, A4, A5 and A6).

Figure 2:
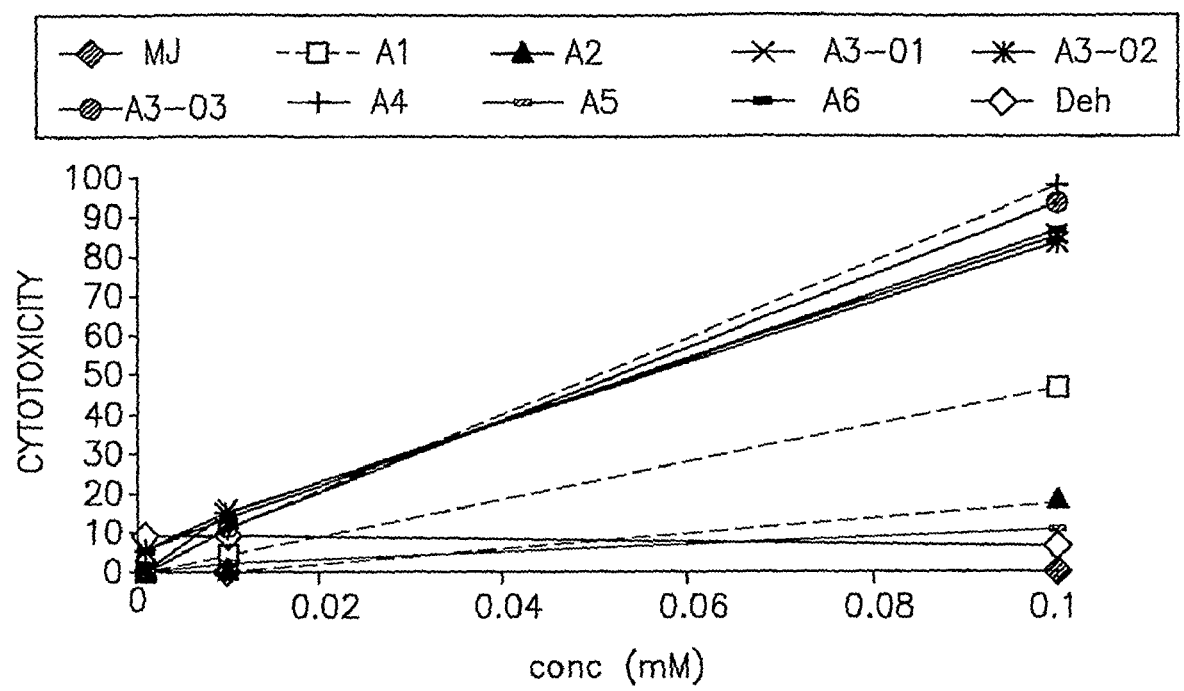
FIG. 2: shows the cytotoxic activity of low concentrations (0.01-0.1 mM) of several compounds of the invention in a lymphoblastic leukemia cell line (Molt-4). Cytotoxicity (%) is plotted against the compound concentration. Methyl jasmonate (MJ) and dihydromethyl jasmonate (Deh) are used as controls.

Accordingly, a second screen was performed at lower concentrations of 0.01-0.1 mM. As shown in FIG. 2, all of the tested compounds were more potent than methyl jasmonate, the most potent derivatives being compounds A1, A3, A4 and A6.

Figure 3:
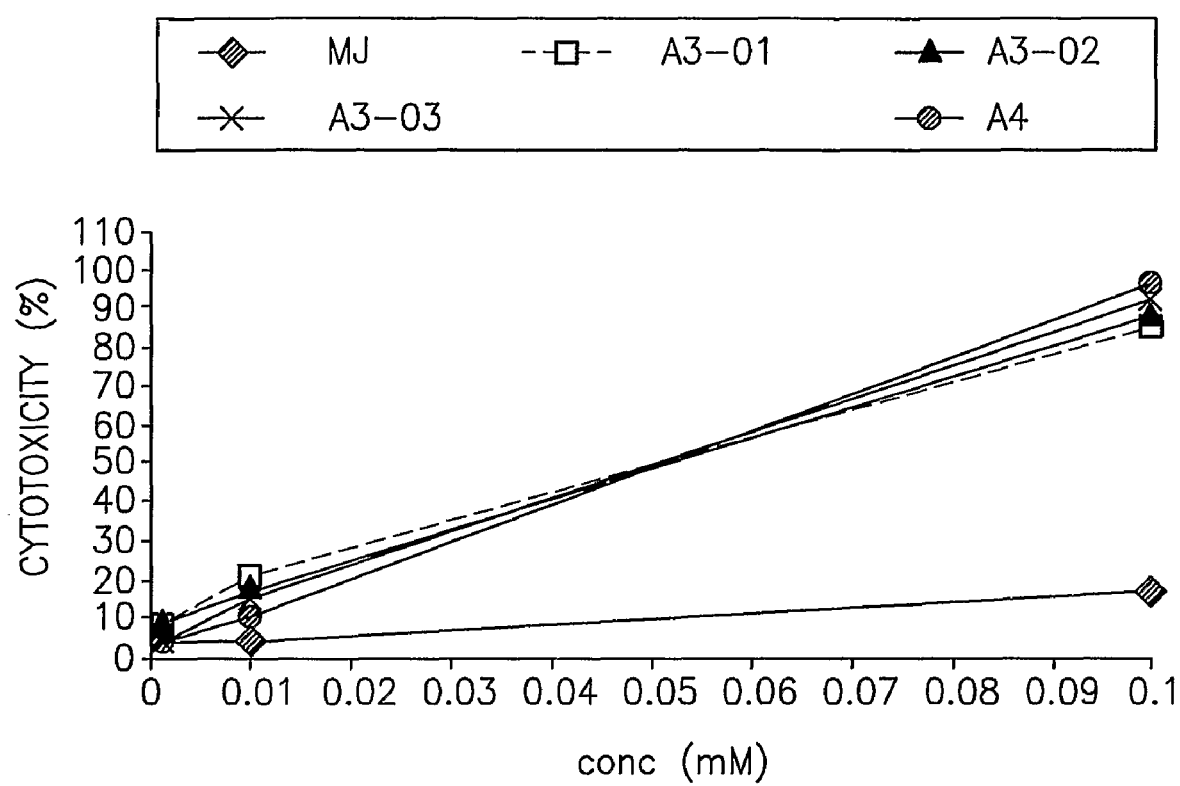
FIG. 3: shows the cytotoxicity of low concentrations (0.01-0.1 mM) of MJ, A3-01, A3-02, A3-03 and A4 towards Molt 4 cells. Two repeats, each in triplicates. Cytotoxicity (%) is plotted against the compound concentration. Methyl jasmonate (MJ) is used as a control. All compounds are more cytotoxic than MJ.

In a third screen, the most potent compounds A3 and A4 were shown to be significantly more potent than methyl jasmonate. The results summarizing the cytotoxicity of the compounds are summarized in FIG. 3 and Table 1. Each repeat was done in triplicate.

TABLE 1

Cytotoxicity of Jasmonate Derivatives in Molt-4 Cells at different concentrations (% of inhibition compared to control)

| (mM) | MJ | A3-01 | A3-02 | A3-03 | A4 |
|---|---|---|---|---|---|
| 0.001 | 6(±8) | 8(±6) | 10(±5) | 4(±5) | 4(±5) |
| 0.01 | 5(±6) | 20(±7) | 18(±5) | 15(±6) | 10(±0) |
| 0.1 | 17(±15) | 85(±5) | 88(±6) | 93(±2) | 96(±2) |

Example 2

Compounds A3 and A4 are Selective Against Cancer Cells

Experimental Set Up:

Molt-4 (leukemia) cells (at $2.5 \times 10^4$/ml), and normal peripheral blood lymphocytes (PBL, at $2 \times 10^5$/ml) were incubated in 96-well plates for one day in the presence of different concentrations of methyl jasmonate, (MJ—disclosed in U.S. Pat. No. 6,469,061), and compounds A3 and A4 of the present invention at concentrations: of 0.001, 0.01, 0.1 and 0.5 mM. In some experiments, PBL were pre-incubated with 0.8 μg/ml phytohemagglutinin (PHA)+5 ng/ml TPA for 48 24 hours, to induce entrance into the cell cycle. These cells proliferate and therefore are similar in that respect to cancer cells, making the comparison more valid. The optical density that represented viable cells was determined as described above.

Results

IC20 and IC50 levels are shown in the following Table 2 below,

Based on previously reported data, MJ is cytotoxic to Molt-4 cells and almost not toxic to normal lymphocytes. Compound A3 was found to be toxic to Molt-4 cells ($IC_{50}$=0.05 mM), while toxicity to normal lymphocytes (−PHA/TPA) was very low ($IC_{20}$=0.03 mM, not reaching $IC_{50}$). Similarly, compound A4 was as found to be toxic to Molt-4 cells ($IC_{50}$=0.045 mM), while in normal lymphocytes with or without PHA/TPA cytotoxicity was ($IC_{20}$=<0.01-0.025 mM, not reaching $IC_{50}$ using concentrations up to 0.5 mM).

Figure 4A:
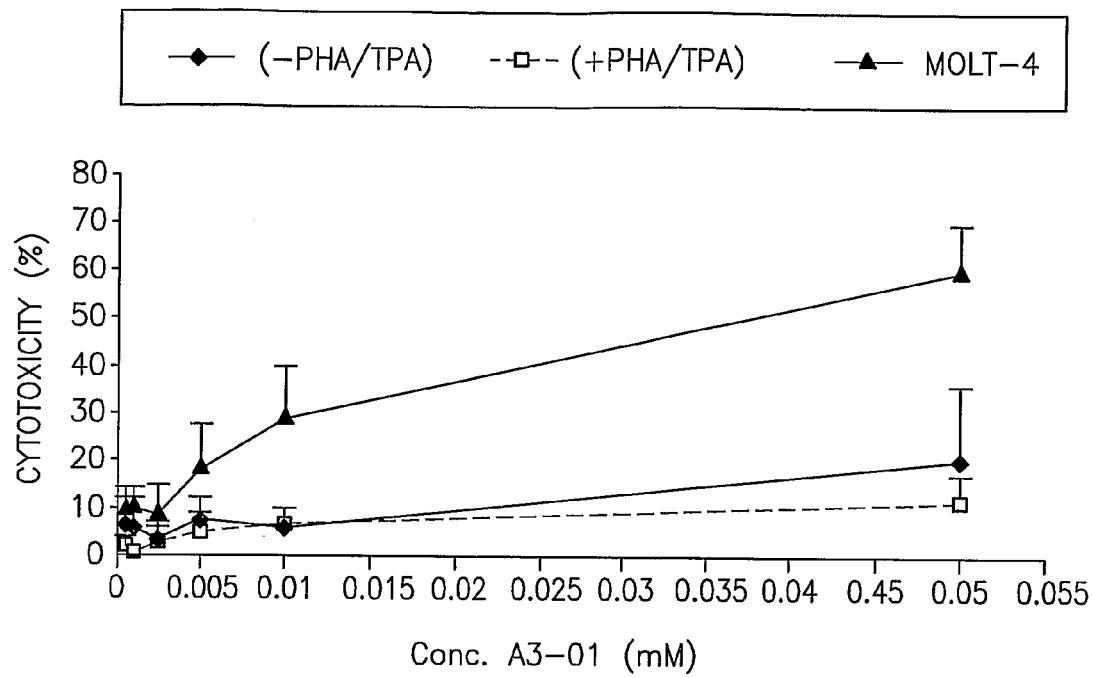
FIG. 4: shows a comparison of the effects of Compound A3 (FIG. 4A) and Compound A4 (FIG. 4B) on normal lymphocytes (PBL) vs. leukemic cells (Molt-4). PBL were incubated with or without PHA and TPA.
Figure 4B:
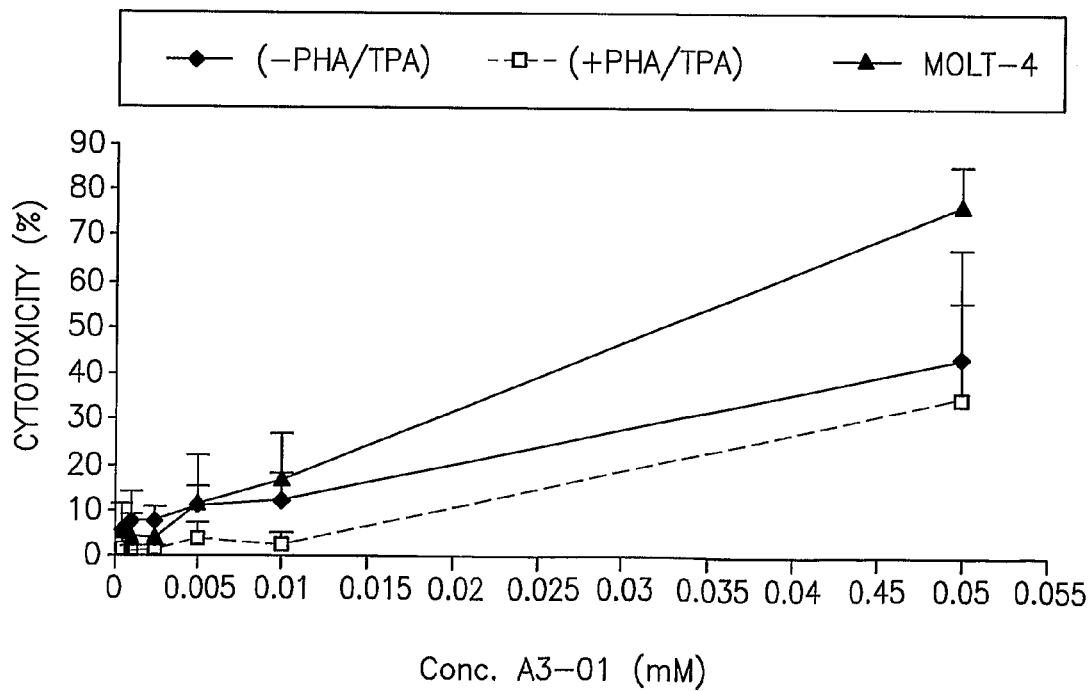

As shown in FIGS. 4A and 4B, there is a comfortable therapeutic window which allows compounds A3 and A4 to kill leukemic cells without exerting a substantial effect on normal lymphocytes. The results demonstrate the ability of the compounds of the present invention to exert a selective cytotoxic effect against cancer cells, without substantially affecting normal cells.

Example 3

Cytotoxicity of Oligomeric Jasmonate Derivatives Towards Leukemia Cells

New MJ-derivatives C1 and C2 were tested for cytotoxicity in 3 cancer cell lines:

A) Molt-4—Human acute lymphoblastic leukemia cell-line
B) CT26—Murine colon carcinoma cell-line
C) MCF7—Human breast adenocarcinoma cell-line The new derivatives were also tested on normal lymphocytes (PBL) obtained from healthy donors. The experimental set up as well as IC50 values obtained for the different cell lines are listed below.

Experimental Set Up:

Mononuclear cells were isolated from peripheral blood of healthy donors by ficoll-hypaque density gradient centrifugation. The mononuclear cells were allowed to adhere to plastic dishes to remove macrophages. Cell densities were as follows: Molt-4 (at $2.5 \times 10^4$ cells in 100 μL per well), CT26 (at $5 \times 10^3$ cells in 100 μL per well), MCF7 (at $5 \times 10^3$ cells in 100 μL per well) and PBL (at $1.5 \times 10^5$ cells in 100 μL per well) well seeded in 96-well plates. Adherent cells (CT26 and MCF7) were allowed to adhere over-night.

MJ-derivatives were added at concentration ranging from 0.005-0.5 mM for 24 hours. Each experimental point was performed in triplicates. Untreated cells were used as control. The MJ-derivatives were prepared stock solutions as described above.

Results

IC50 values for the various cell lines are shown in Table 3 below for compounds C1 and C2. Compound C3 was not soluble

TABLE 2

|  | $IC_{20}$ (mM) | | | $IC_{50}$ (mM) | | |
|---|---|---|---|---|---|---|
|  | Molt-4 | −PHA/TPA | +PHA/TPA | Molt-4 | −PHA/TPA | +PHA/TPA |
| MJ* | 0.03-0.05 | >0.5 | >0.5* | 0.1-0.5 | >0.5* | >0.5* |
| A3** | 0.01 | 0.03 | 0.07 | 0.05 | 0.25 | 0.3 |
| A4** | <0.01 | <0.01 | 0.025 | 0.045 | 0.045 | 0.06 |

*~20 repeats
**A3 and A4, two repeats

TABLE 3

| Compound | IC50 in Molt-4 (mM) | IC50 in CT-26 (mM) | IC50 in MCF-7 (mM) | IC50 in PBL |
|---|---|---|---|---|
| C1 | 0.087 ± 0.055 | 0.273 ± 0.197 | 0.160 ± 0.085 | 0.290 ± 0.170 |
| C2 | 0.080 ± 0.014 | 0.455 ± 0.021 | >0.500 | >0.500 |

Example 4

Selectivity of Jasmonate Derivative Compound B3

Cytotoxicity of compound B3 was evaluated in 1) Molt 4 cells (an in-vitro model for transformed cells); 2) PBL (an ex vivo model for normal cells); and 3) PBL CLL—Peripheral blood lymphocytes collected from chronic lymphocytic leukemia patients (an ex vivo model for ex vivo transformed cells).

Experimental Set Up

Mononuclear cells were isolated from peripheral blood of healthy donors and treated as described above. The non-adherent PBL were pre-incubated without PHA and TPA. Molt-4 and PBL cells were seeded in 96-well plates as described above.

Compound B3 was added at concentration ranging from 0.0025-1 mM for 24 hours. The number of repeats for each experiment is indicated by n. Untreated cells were used as control. Compound B3 was prepared as a stock of 100 mM in 100% DMSO and dilutions in medium were prepared as described above. Optical density and percentage of Cytotoxicity were determined as described above.

Figure 5:
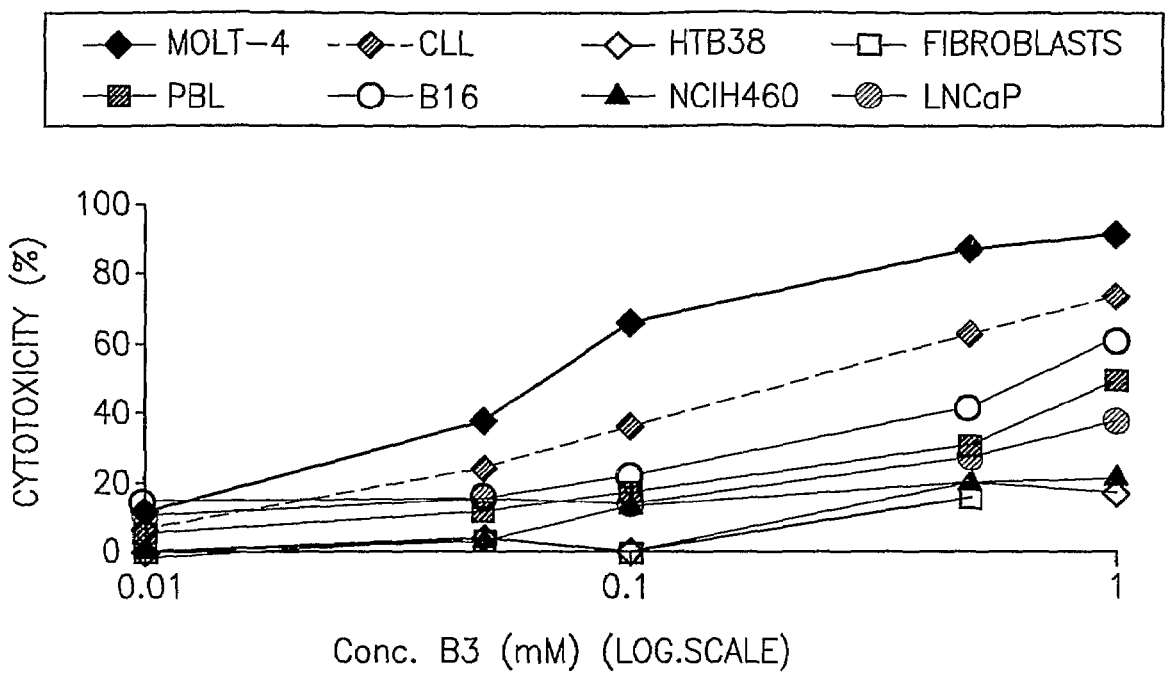
FIG. 5: shows the cytotoxic activity of increasing concentrations (0.0025-0.5 mM) of compound B3 in several cell lines including lymphoblastic leukemia cells (Molt-4), chronic lymphocytic leukemia cells (CLL) and peripheral blood lymphocytes (PBL). Cells were grown without PHA/TPA. Cytotoxicity (%) is plotted against the concentration of compound B3.
Figure 6:
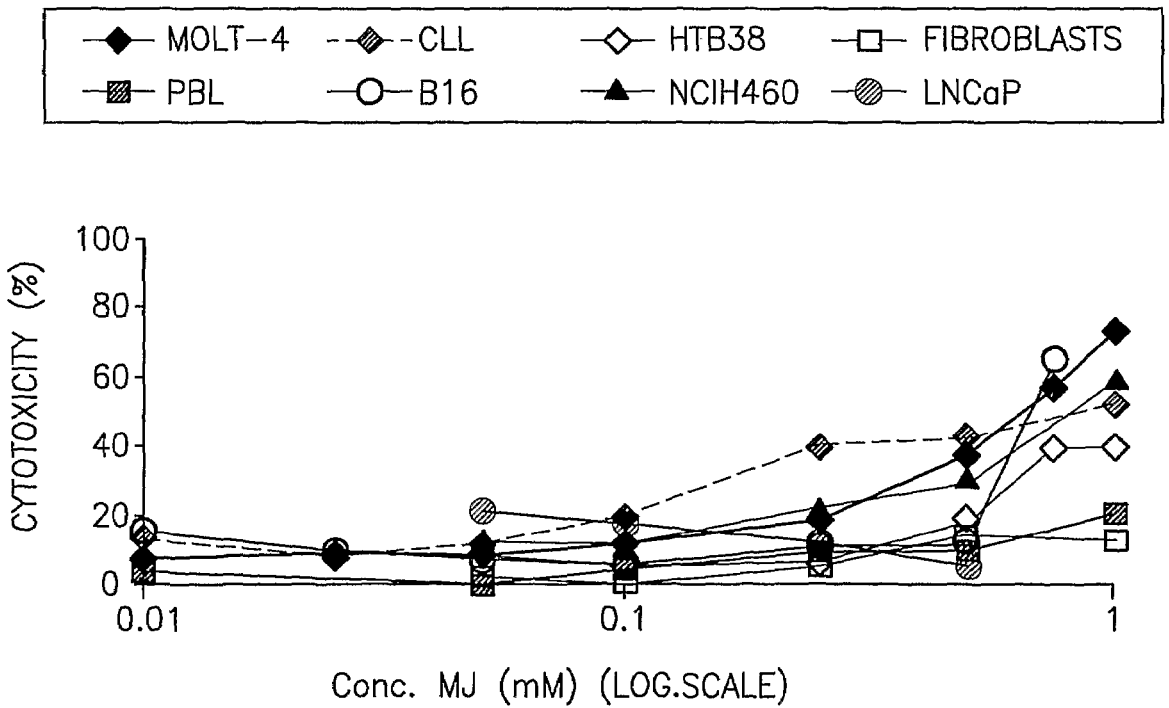
FIG. 6: shows the cytotoxic activity of increasing concentrations (0.0025-0.5 mM) of methyl jasmonate (MJ) in several cell lines including lymphoblastic leukemia cells (Molt-4), chronic lymphocytic leukemia cells (CLL) and peripheral blood lymphocytes (PBL). PBL cells were grown without PHA/TPA. Cytotoxicity (%) is plotted against the concentration of methyl jasmonate (MJ).

As shown in FIG. 5, compound B3 exhibits selective cytotoxicity towards cancer cells at the various tested concentrations tested. Table 4 lists the concentration (mM) of compound B3 that is needed for 50% cytotoxicity in the different cell cultures (IC50).

TABLE 4

IC50 values of B3 in Cancer and Normal cell cultures

| Cell line | Organism | Origin of cell line | n= | IC50 (mM) |
|---|---|---|---|---|
| Molt-4 | Human | T lymphoblast, acute lymphoblastic leukemia | 12 | 0.07 |
| CLL | Human | PBL, chronic lymphocytic leukemia | 14 | 0.25 |
| MDA* | Human | Epithelial, mammary gland, adenocarcinoma | | |
| NCI H460 | Human | Lung, carcinoma, large cell lung cancer | 3 | >1 |
| B16 | Mouse | Skin, melanoma | 6 | 0.7 |
| HTB38 | Human | Epithelial, Colon, colorectal adenocarcinoma | 3 | >1 |
| PC3 | Human | Epithelial, prostate, adenocarcinoma | | |
| LNCaP | Human | Epithelial, prostate, carcinoma | 4 | >1 |
| PBL | Human | PBL, healthy donors | 12 | 1 |
| Fibroblasts | Human | Fibroblasts | 2 | >0.5 |

MDA* - (MDA-MB-231)

Conclusions

Compound B3 has an IC50 of 0.07 mM in the sensitive cell line Molt-4. The next most sensitive cells were PBL derived from CLL patients.

The results demonstrate the ability of compound B3 to exert a selective cytotoxic effect against cancer cells, without substantially affecting normal cells.

Example 5

Cytotoxicity of Different Batches of Compound B3 Towards Molt-4 Cell Line

Comparing different batches of the compound revealed that all preparations had the same cytotoxicity in Molt-4. The IC50 values in Molt-4 cells for B3 were 0.06 mM in average. For cytotoxicity evaluation in different cell lines B3-IV was used.

TABLE 5

| Compound | n= | IC50 (mM) |
|---|---|---|
| Methyl jasmonate (MJ) | 61 | 0.6 |
| Compound B3 (III) | 5 | 0.06 |
| Compound B3 (IV) | 3 | 0.05 |
| Compound B3 (V) | 4 | 0.08 |

Example 6

Effect of Jasmonate Derivatives in Ex Vivo and In Vivo Model Systems

The effect of jasmonate derivatives are studied Ex-vivo on blood from healthy donors and from CLL patients, and in an in-vivo model system by IV and PO administration to mice in several mice cancer models (B16, CT26, and EL4).

The compounds are administered in pharmaceutical compositions, as summarized in Table 6 below. Formula I is the currently preferred formula.

TABLE 6

| | Jasmonate Derivative | PC | EtOH | PG | AAA | A-TPh |
|---|---|---|---|---|---|---|
| Control | 0 | 30 mg/ml | 20 μg/ml | 20 μg/ml | 1 mg/ml | 0.4 mg/ml |
| Formula I | 22 mM (5 μg/ml) | 30 mg/ml | 20 μg/ml | 20 μg/ml | 1 mg/ml | 0.4 mg/ml |
| Formula II | 22 mM (5 μg/ml) | 30 mg/ml | 20 μg/ml | 20 μg/ml | 5 mg/ml | 0.4 mg/ml |
| Formula III | 22 mM (5 μg/ml) | 30 mg/ml | 20 μg/ml | 20 μg/ml | 10 mg/ml | 0.4 mg/ml |

TABLE 6-continued

| | Jasmonate Derivative | PC | EtOH | PG | AAA | A-TPh |
|---|---|---|---|---|---|---|
| Formula IV | 22 mM (5 µg/ml) | 30 mg/ml | 20 µg/ml | 20 µg/ml | 1 mg/ml | 1 mg/ml |
| Formula V | 22 mM (5 µg/ml) | 30 mg/ml | 20 µg/ml | 20 µg/ml | 2 mg/ml | 0.4 mg/ml |

EtOH - Alcohol
PG - Propylene Glycol
PC - Lecithin
AAP - Ascorbil - Palmitate
α-TPh - alpha Tocopheryl Polyethylene Glycol

Example 7

Effect of Methyl Jasmonate and Compound B3 on ATP Depletion

Figure 7:
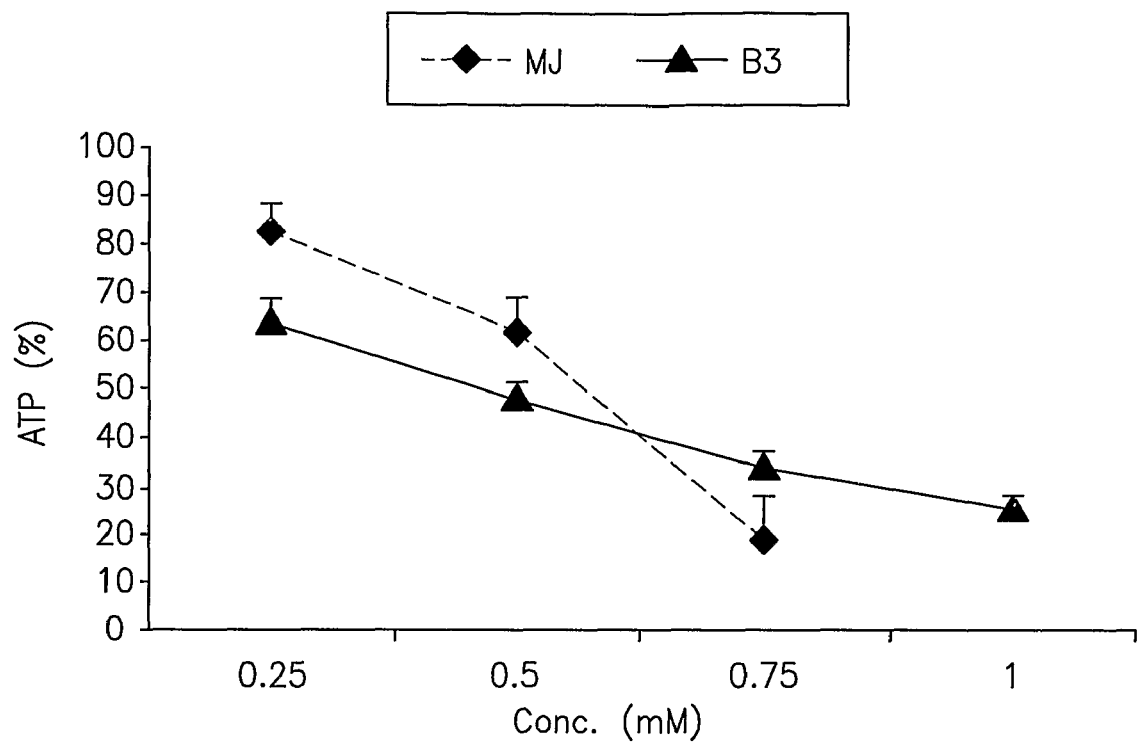
FIG. 7: shows the depletion of ATP levels in the Molt-4 cell line over 1 hr with different concentrations of compound B3 and methyl jasmonate (MJ). ATP depletion (%) is plotted against concentration of B3 and methyl jasmonate (MJ).
Figure 8:
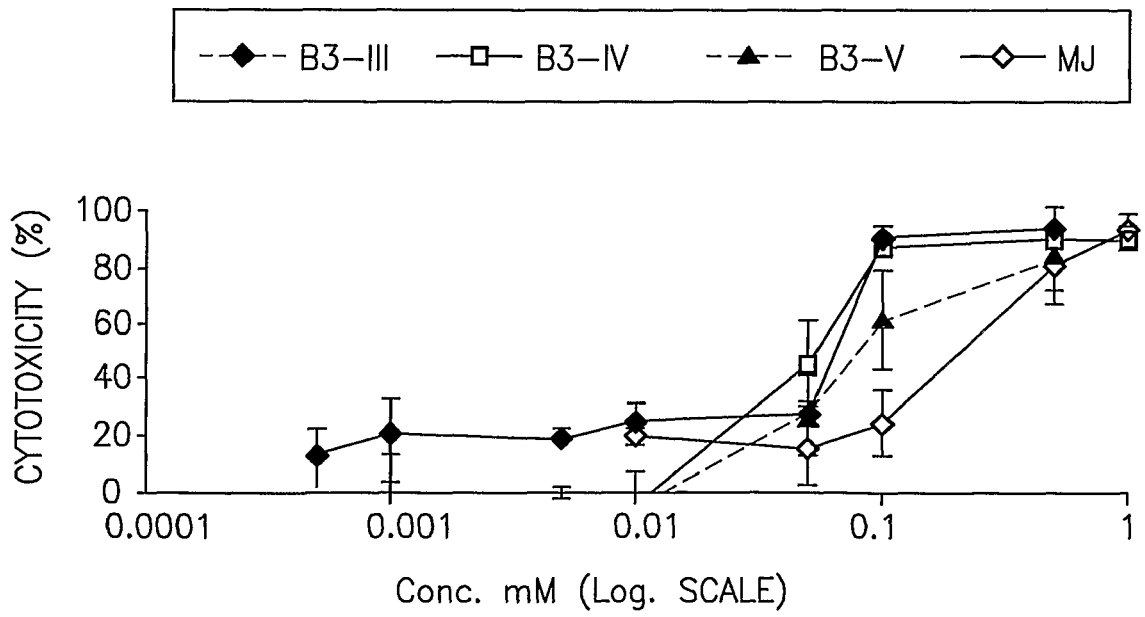
FIG. 8: shows the cytotoxicity of different batches of compound B3 and one batch of methyl jasmonate (MJ) towards Molt-4 cells. Cytotoxicity (%) is plotted against different concentrations of the different B3 batches and one methyl jasmonate (MJ) batch.

The effect of methyl jasmonate and compound B3 on ATP level depletion is studied in the Molt 4 cell line using ATP kit and luminometer (Cell titer—Glo Luminescent, cell viability assay, Promega, code G7571, Ref.)
Cell preparation: Cells (Molt 4) were seeded in 96-well opaque-walled plates. The number of cells (in a volume of 100 µL/well) was: 5×10$^4$ cells/well. Control wells contained 100 µL medium without cells (background luminescence) Incubations were performed at 37° C., 6% $CO_2$, using the following culture medium: RPMI 1640, 10% FCS, 2 mM L-Glutamine and penicillin 200 U/ml+200 µg/ml streptomycin or equivalent. For the cell viability assay, cells were incubated for 12 min-24 hr. in the absence or presence of methyl jasmonate or several jasmonate derivatives of the present invention at 0.05-4 mM.
Reagent Preparation The CellTiter-Glo® buffer and the lyophilized substrate were thawed and equilibrated to room temperature. The buffer was mixed with the substrate by vortexing for 1 minute.
Treatment: Methyl jasmonate was prepared as a stock of 500 mM in 100% ethanol. Dilutions were performed in the culture medium. Same concentration of ethanol (10%) in each dilution was maintained, resulting in the final concentration of ethanol in each well being 0.6%. This concentration of ethanol by itself did not affect the viability of the Molt-4 cell line. Stock solutions of compound B3 in DMSO were prepared as described above. Compound B3 was added in an identical volume, i.e., 6 µL, to each well, yielding the relevant final concentrations (0.05, 0.1, 0.25, 0.5, 1, 2, 3, 4 mM). Each experimental point is performed in n times, Table 5 lists the IC50 values thus obtained for compound B3 and methyl jasmonate.
The plates were equilibrated to room temperature [25° C.] for 30 min. An ATP standard curve was prepared by preparing 1 µM ATP in culture medium. A 10 fold serial dilution is made in culture medium [1 µM-10 nM]. 100 µL were transferred to each well. 100 µL volume of CellTiter-Glo® reagent was added to each well (with or without cells). The contents were mixed for 2 min. on an orbital shaker to induce cell lysis. The plates were allowed to incubate at 25° C. for 10 min in the Luminoskan to stabilize luminescence signal. Results were read through Record luminescence [Thermo-Luminoskan Ascent] or equivalent, with integration time of 2000 m. seconds per well and blanking time 5%. Each experiment was performed 3 times. Percent of cytotoxicity was determined described above.
The results are shown in FIG. 7 and in table 7. As shown, the IC50 causing depletion of ATP over 1 hr. exposure was similar to that of methyl jasmonate. The IC50 causing cytotoxicity over 24 hr. incubation of Molt-4 with compound B3 was 10 folds lower compared to ATP depletion and methyl jasmonate cytotoxicity. Without wishing to be bound by any particular mechanism or theory, it is contemplated that depletion of ATP might be an additional pathway of compound B3 effect on cell cytotoxicity.

TABLE 7

| Compound | n= | IC50 (mM) |
|---|---|---|
| Methyl Jasmonate | 6 | 0.5 |
| Compound B3 | 3 | 0.5 |

Example 8

Synthesis

Methyl jasmonate was purchased from Aldrich.
Compound C3:

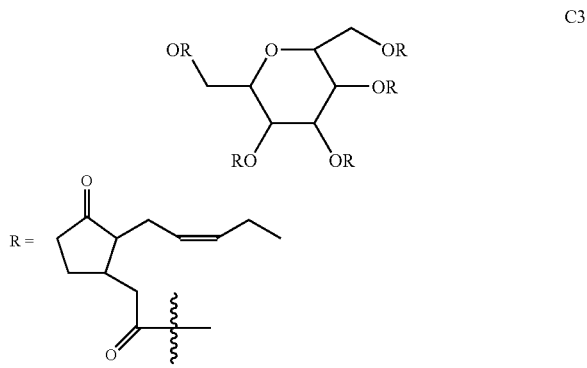

To a stirred solution of glucose (144 mg, 0.799 mmol) in pyridine (5 mL), at 0° C. under argon atmosphere was added dropwise a solution of Jasmonyl chloride (1.3 gr, 5.70 mmol) in dry $CH_2Cl_2$ (10 mL) and the reaction mixture was stirred for 0.5 hr at 0° C., allowed to warm up to room temperature and further stirred for 12 hr. The solvent was then evaporated and the residue diluted with EtOAc and washed with saturated aq. $NaHCO_3$ (×2). The organic layer was washed with brine, dried over $Na_2SO_4$ and concentrated in vacuo. The residue was purified by Sephadex LH20 ($CHCl_3$/methanol 1:1) affording compound C3 (379 mg, 36%) as a brownish oil.
While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

Compound B3:

To a stirred solution of jasmonic acid (80 mg, 0.381 mmol), catalytic amount of DMAP and compound 1 (77 mg 0.393 mmol) in dry CH$_2$Cl$_2$ (10 mL) at 0° C., under argon atmosphere, was added EDCI (109 mg, 0.571 mmol). The mixture was stirred for 2 hr at 0° C., allowed to warm up to room temperature and then stirred for further 12 hr. The mixture was poured into saturated aq. NaHCO$_3$ (2×20 mL) and extracted with CH$_2$Cl$_2$ (×3). The combined organic layer was washed with brine, dried over Na$_2$SO$_4$ and concentrated in vacuo. The residue was purified by VLC (EtOAc/petroleum ether 1:9) affording compound 10 (91 mg, 62%) as a colorless oil.

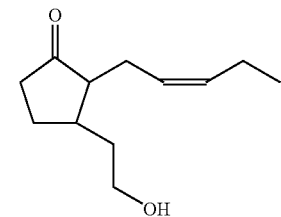

1

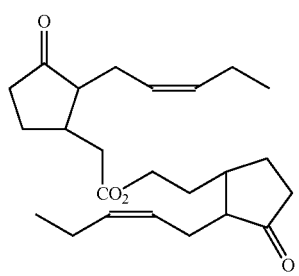

B3

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A compound represented by the structure of Formula I or Formula IIA:

A) a compound of Formula I:

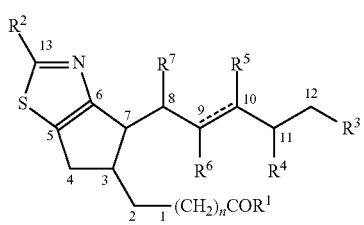

(I)

wherein n is 0, 1, or 2;

R$^1$ is selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, a natural or unnatural amino acid, a peptide, OR$^8$ and NR$^{9a}$R$^{9b}$;

R$^2$ is selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, OR$^8$, NR$^{9a}$R$^{9b}$, NHCOR$^{10}$ and NHSO$_2$R$^{11}$;

R$^3$, R$^4$, R$^5$, R$^6$ and R$^7$ are each independently selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, OR$^8$ and NR$^{9a}$R$^{9b}$;

wherein the bond between C$_9$ and C$_{10}$ can be a single or a double bond; and R$^8$, R$^{9a}$, R$^{9b}$, R$^{10}$ and R$^{11}$, are each independently selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, glucosyl, or R$^{9a}$ and R$^{9b}$ can together with the nitrogen to which they are attached form an unsubstituted or substituted heterocyclic or heteroaromatic ring optionally containing one or more additional heteroatom selected from O, N and S;

including salts, hydrates, solvates, optical isomers, geometrical isomers, enantiomers, diastereomers, and mixtures thereof;

B) a compound of Formula IIA:

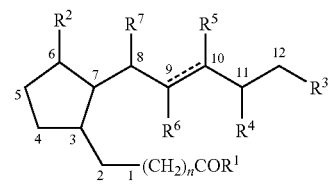

(IIA)

wherein n is independently at each occurrence 0, 1, or 2;

R$^1$ is a group of the formula:

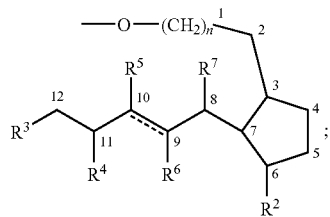

R$^2$ is independently at each occurrence selected from the group consisting of hydrogen, unsubstituted or substituted C$_1$-C$_{12}$ alkyl, unsubstituted or substituted C$_3$-C$_8$ cycloalkyl, unsubstituted or substituted aryl, unsubstituted or substituted heteroaryl, OR$^8$, oxo and NR$^{9a}$R$^{9b}$;

R$^3$, R$^4$, R$^5$, R$^6$ and R$^7$ are each independently at each occurrence selected from the group consisting of hydrogen, unsubstituted or substituted C$_1$-C$_{12}$ alkyl, unsubstituted or substituted $C_3$-$C_8$ cycloalkyl, unsubstituted or substituted aryl, unsubstituted or substituted heteroaryl, $OR^8$ and $NR^{9a}R^{9b}$;

wherein the bond between $C_9$ and $C_{10}$ can independently at each occurrence be a single or a double bond; and $R^8$, $R^{9a}$ and $R^{9b}$ are each independently at each occurrence selected from the group consisting of hydrogen, unsubstituted or substituted $C_1$-$C_{12}$ alkyl, unsubstituted or substituted $C_3$-$C_8$ cycloalkyl, unsubstituted or substituted aryl, unsubstituted or substituted heteroaryl, glucosyl, or $R^{9a}$ and $R^{9b}$ can together with the nitrogen to which they are attached form an unsubstituted or substituted heterocyclic or heteroaromatic ring optionally containing one or more additional heteroatom selected from O, N and S;

including salts, hydrates, solvates, optical isomers, geometrical isomers, enantiomers, diastereomers, and mixtures thereof.

2. The compound of claim 1, wherein the compound is represented by the structure of Formula I.

3. The compound of claim 2, wherein $R^1$ is OH, $OCH_3$, or $NR^{9a}R^{9b}$, wherein $R^{9a}$ is hydrogen and $R^{9b}$ is selected from the group consisting of unsubstituted or substituted $C_1$-$C_{12}$ alkyl, unsubstituted or substituted $C_3$-$C_8$ cycloalkyl, unsubstituted or substituted aryl, and unsubstituted or substituted heteroaryl, or $R^{9a}$ and $R^{9b}$ together with the nitrogen to which they are attached form an unsubstituted or substituted heterocyclic or heteroaromatic ring optionally containing one or more additional heteroatom selected from O, N and S.

4. The compound of claim 2, wherein $R^2$ is selected from the group consisting of aryl, $NR^{9a}R^{9b}$, $NHCOR^{10}$, $NHSO_2R^{11}$, phenyl, and $NHCOR^{10}$ wherein $R^{10}$ is a $C_1$-$C_{12}$ alkyl substituted with an aryl or heteroaryl.

5. The compound of claim 2, wherein the bond between $C_9$ and $C_{10}$ is a single bond, and $R^3$, $R^4$, $R^5$, $R^6$ and $R^7$ are each hydrogen.

6. The compound of claim 2, wherein the compound is selected from the group consisting of:

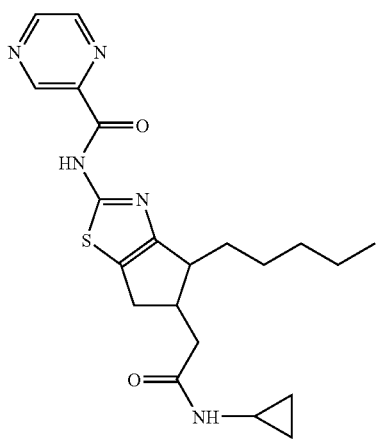

A1

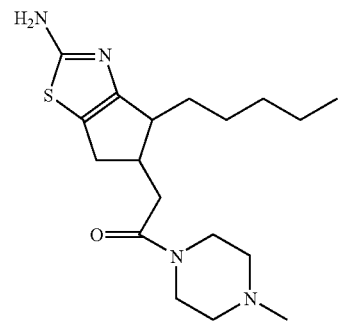

A2

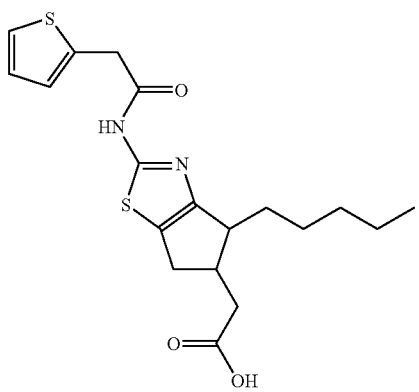

A3

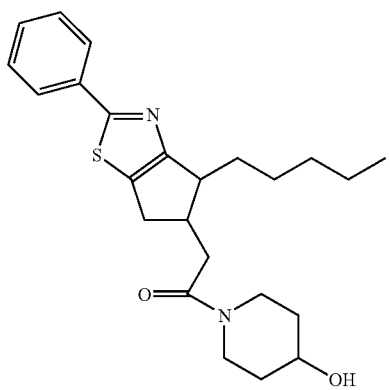

A4

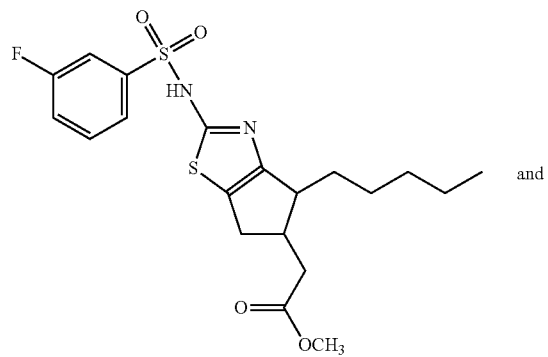

A5 and

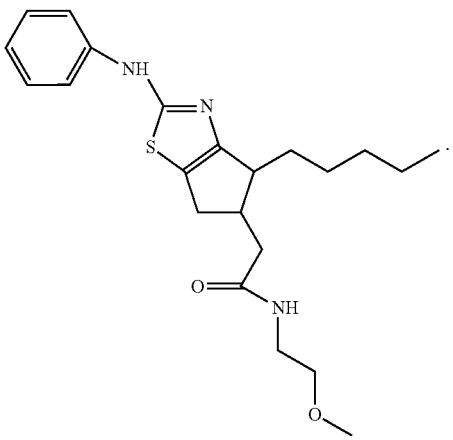
A6

7. The compound of claim 1, wherein the compound is represented by the structure of Formula IIA.

8. The compound of claim 7, wherein $R_2$ is oxo.

9. The compound of claim 7, wherein the bond between $C_9$ and $C_{10}$ is a double bond, and $R^3$, $R^4$, $R^5$, $R^6$ and $R^7$ are each hydrogen.

10. The compound of claim 7, which is represented by the structure of Formula III:

(III)

11. The compound of claim 7, which is represented by the structure of Formula B3:

B3

12. A pharmaceutical composition comprising a compound of claim 1 as an active ingredient, and a pharmaceutically acceptable carrier.

13. The pharmaceutical composition of claim 12, wherein the composition is in a form suitable for oral parenteral, transdermal, topical, or rectal administration, administration by inhalation, administration via a suppository or administration via dialysis.

14. A method for inhibiting cancer cell proliferation, comprising the step of contacting said cancer cells with a therapeutically effective amount of a compound according to claim 1, wherein the cancer is selected from the group consisting of: lymphoproliferative disorders, breast cancer, lung cancer, myeloma, leukemia, lymphoma, lymphoblastic leukemia, lymphocytic leukemia, melanoma, adenocarcinoma, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, and metastases of all the above.

15. A method for inhibiting cancer cell proliferation, comprising the step of contacting said cancer cells with a therapeutically effective amount of a compound according to claim 1, wherein the cancer is selected from the group consisting of: breast cancer, leukemia, lymphoma, lymphocytic leukemia, lymphoblastic leukemia, adenocarcinoma, lung carcinoma, skin cancer, melanoma, colon cancer, colorectal adenocarcinoma, and metastases of all the above.

16. A method for treating cancer in a subject, comprising the step of administering to the subject a therapeutically effective amount of a compound according to claim 1, wherein the cancer is selected from the group consisting of: lymphoproliferative disorders, breast cancer, lung cancer, myeloma, leukemia, lymphoma, lymphoblastic leukemia, lymphocytic leukemia, melanoma, adenocarcinoma, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, and metastases of all the above.

17. The method of claim 16, wherein the cancer is a mammalian cancer or a human cancer.

18. A method for treating cancer in a subject, comprising the step of administering to the subject a therapeutically effective amount of a compound according to claim 1, wherein the cancer is selected from the group consisting of: breast cancer, leukemia, lymphoma, lymphocytic leukemia, lymphoblastic leukemia, adenocarcinoma, lung carcinoma, skin cancer, melanoma, colon cancer, colorectal adenocarcinoma, and metastases of all the above.

19. The method of claim 18, wherein the cancer is a mammalian cancer or a human cancer.

* * * * *